United States Patent
Shih et al.

(10) Patent No.: US 9,897,597 B2
(45) Date of Patent: Feb. 20, 2018

(54) HIGH-THROUGHPUT STRUCTURE DETERMINATION USING NUCLEIC ACID CALIPERS

(71) Applicants: Children's Medical Center Corporation, Boston, MA (US); Dana-Farber Cancer Institute, Inc., Boston, MA (US)

(72) Inventors: William M. Shih, Cambridge, MA (US); Wesley Philip Wong, Cambridge, MA (US)

(73) Assignees: Children's Medical Center Corporation, Boston, MA (US); Dana-Farber Cancer Institude, Inc., Boston, MA (US)

( * ) Notice: Subject to any disclaimer, the term of this patent is extended or adjusted under 35 U.S.C. 154(b) by 0 days.

(21) Appl. No.: 15/305,399

(22) PCT Filed: Apr. 23, 2015

(86) PCT No.: PCT/US2015/027290
§ 371 (c)(1),
(2) Date: Oct. 20, 2016

(87) PCT Pub. No.: WO2015/164602
PCT Pub. Date: Oct. 29, 2015

(65) Prior Publication Data
US 2017/0045506 A1  Feb. 16, 2017

Related U.S. Application Data

(60) Provisional application No. 61/982,914, filed on Apr. 23, 2014.

(51) Int. Cl.
*G01N 33/543* (2006.01)
*C12Q 1/68* (2018.01)

(52) U.S. Cl.
CPC ......... *G01N 33/54333* (2013.01); *C12Q 1/68* (2013.01); *C12Q 1/6804* (2013.01); *G01N 2458/10* (2013.01)

(58) Field of Classification Search
None
See application file for complete search history.

(56) References Cited

U.S. PATENT DOCUMENTS

| | | |
|---|---|---|
| 2012/0149129 A1 | 6/2012 | Pai et al. |
| 2012/0238738 A1 | 9/2012 | Hendrickson |
| 2013/0288349 A1 | 10/2013 | Wong et al. |

FOREIGN PATENT DOCUMENTS

WO    WO2013059044    * 4/2013

OTHER PUBLICATIONS

Halvorsen et al., Massively parallel single-molecule manipulation using centrifugal force, Biophys J. Jun. 2, 2010;98(11):L53-5.*
Halvorsen et al., Nanoengineering a single-molecule mechanical switch using DNA self-assembly, Nanotechnology. Dec. 9, 2011;22(49):494005.*
Claridge et al., Electrons, photons, and force: quantitative single-molecule measurements from physics to biology, ACS Nano. Feb. 22, 2011;5(2):693-729.*
De Vlaminck et al., Magnetic forces and DNA mechanics in multiplexed magnetic tweezers, PLoS One. 2012;7(8):e41432. Epub Aug. 3, 2012.*
Kim et al., A high-resolution magnetic tweezer for single-molecule measurements, Nucleic Acids Res. Nov. 2009; 37(20): e136, Published online Sep. 3, 2009.*
Robison et al., High-throughput single-molecule studies of protein-DNA interactions, FEBS Lett. Oct. 1, 2014;588(19):3539-46. Epub May 21, 2014.*
Ackbarow et al., Strength and robustness of protein materials. Encyclopedia of Nanoscience and Nanotechnology. 2011;23:349-87.
Dessinges et al. Stretching single stranded DNA, a model polyelectrolyte. Phys Rev Lett. Dec. 9, 2002;89(24):248102(1-4), Epub Nov. 22, 2002.
Lansdorp et al., A high-speed magnetic tweezer beyond 10,000 frames per second. Rev Sci Instrum. Apr. 2013;84(4):044301(1-5), doi:10.1063/1.4802678.
Otto et al., Real-time particle tracking at 10,000 fps using optical fiber illumination. Opt. Express. Oct. 25, 2010;18(22):22722-33, doi: 10.1364/OE.18.022722.
Plesa et al., Ionic permeability and mechanical properties of DNA origami nanoplates on solid-state nanopores. ACS Nano. Jan. 28, 2014;8(1):35-43, doi: 10.1021/nn405045x., Epub Dec. 5, 2013.
Schmied et al. DNA origami—based standards for quantitative fluorescence microscopy. Nat. Protocols. 2014;9(6), 1367-91, doi: 10.1038/nprot.2014.079, Epub May 15, 2014 submitted in 2 parts.
Wagenbauer et al., Quantifying quality in DNA self-assembly. Nat Commun. Apr. 22, 2014; 5:3691, doi: 10.1038/ncomms4691, 7 pages.
Wong et al., Exploring reaction pathways of single-molecule interactions through the manipulation and tracking of a potential-confined microsphere in three dimensions. Mat Res Soc Symp Proc. 2004. vol. 790: P5.1.1-5.1.12, Cambridge Univ. Press, Symposium held Dec. 1-4, 2003, Boston, MA, USA.
Yurke et al., Using DNA to power nanostructures. Genetic Programming and Evolvable Machines. 2003;4:111-22.
Douglas et al. Self-assembly of DNA into nanoscale three-dimensional shapes. Nature 459, 414-418 (2009).
Halvorsen et al., Massively parallel single-molecule manipulation using centrifugal force. Biophys J. Jun. 2010;98:L53-55.

(Continued)

*Primary Examiner* — Aaron Priest
(74) *Attorney, Agent, or Firm* — Wolf, Greenfield & Sacks, P.C.

(57) ABSTRACT

Provided herein are compositions and methods for determining the structure of individual targets using nucleic acid caliper by determining long-range distances within such targets.

28 Claims, 16 Drawing Sheets

(56) References Cited

OTHER PUBLICATIONS

Heinrich et al., Imaging biomolecular interactions by fast three-dimensional tracking of laser-confined carrier particles. Langmuir. 2008;24(4):1194-1203.
Pinheiro et al., Challenges and opportunities for structural DNA nanotechnology. Nat Nanotechnol. Dec. 2011;6:763-72.
Schmied et al. DNA origami-based standards for quantitative fluorescence microscopy. Nat. Protocols 9, 1367-1391 (2014).
Sitters et al. Acoustic force spectroscopy. Nature Methods 12, 47-50 (2015).
Wong et al., The effect of integration time on fluctuation measurements: calibrating an optical trap in the presence of motion blur. Optics Express. Dec. 11, 2006;14(25):12517-31.
Wong, Exploring single-molecule interactions through 3D optical trapping and tracking: from thermal noise to protein refolding. PhD Thesis, Dept. of Physics, Harvard University, Oct. 2006, 136 pages.
Woodside et al. Nanomechanical measurements of the sequence-dependent folding landscapes of single nucleic acid hairpins. Proceedings of the National Academy of Sciences 103, 6190-6195 (2006).
Zhang et al., Control of DNA strand displacement kinetics using toehold exchange. J Am Chem Soc. 2009;131(47):17303-14.
Zhang et al., Optimizing the specificity of nucleic acid hybridization. Nat Chem 4, 208-214 (2012).
Invitation to Pay Additional Fees dated Aug. 13, 2015 for PCT/US2015/027290.
International Search Report and Written Opinion dated Oct. 28, 2015 for PCT/US2015/027290.
International Preliminary Report on Patentability dated Nov. 3, 2016 for PCT/US2015/027290.
Basle et al., Protein chemical modification on endogenous amino acids. Chem Biol. Mar. 26, 2010;17(3):213-27. doi: 10.1016/j.chembiol.2010.02.008.
Kim et al., A high-resolution magnetic tweezer for single-molecule measurements. Nucleic Acids Res. Nov. 2009;37(20):e136. doi: 10.1093/nar/gkp725. Epub Sep. 3, 2009.
Koirala et al., Single-molecule mechanochemical sensing using DNA origami nanostructures. Angew Chem Int Ed Engl. Jul. 28, 2014 53(31):8137-41. doi: 10.1002/anie.201404043. Epub Jun. 16, 2014.
Koussa et al., Protocol for sortase-mediated construction of DNA-protein hybrids and functional nanostructures. Methods. May 15, 2014;67(2):134-41. doi: 10.1016/j.ymeth.2014.02.020. Epub Feb. 22, 2014.
Pfitzner et al., Rigid DNA beams for high-resolution single-molecule mechanics. Angew Chem Int Ed Engl. Jul. 22, 2013;52(30):7766-71. doi: 10.1002/anie.201302727. Epub Jun. 21, 2013.
Extended European Search Report dated Nov. 10, 2017 for Application No. EP 15783027.4.
Halvorsen et al., Nanoengineering a single-molecule mechanical switch using DNA self-assembly. Nanotechnology. Nov. 21, 2011;22(49):494005(1-8).
Koussa et al., DNA nanoswitches: a quantitative platform for gel-based biomolecular interaction analysis. Nat Methods. Feb. 1, 2015;12(2):123-6. Suppl Protocol, 4 pages. Epub Dec. 8, 2014.

* cited by examiner

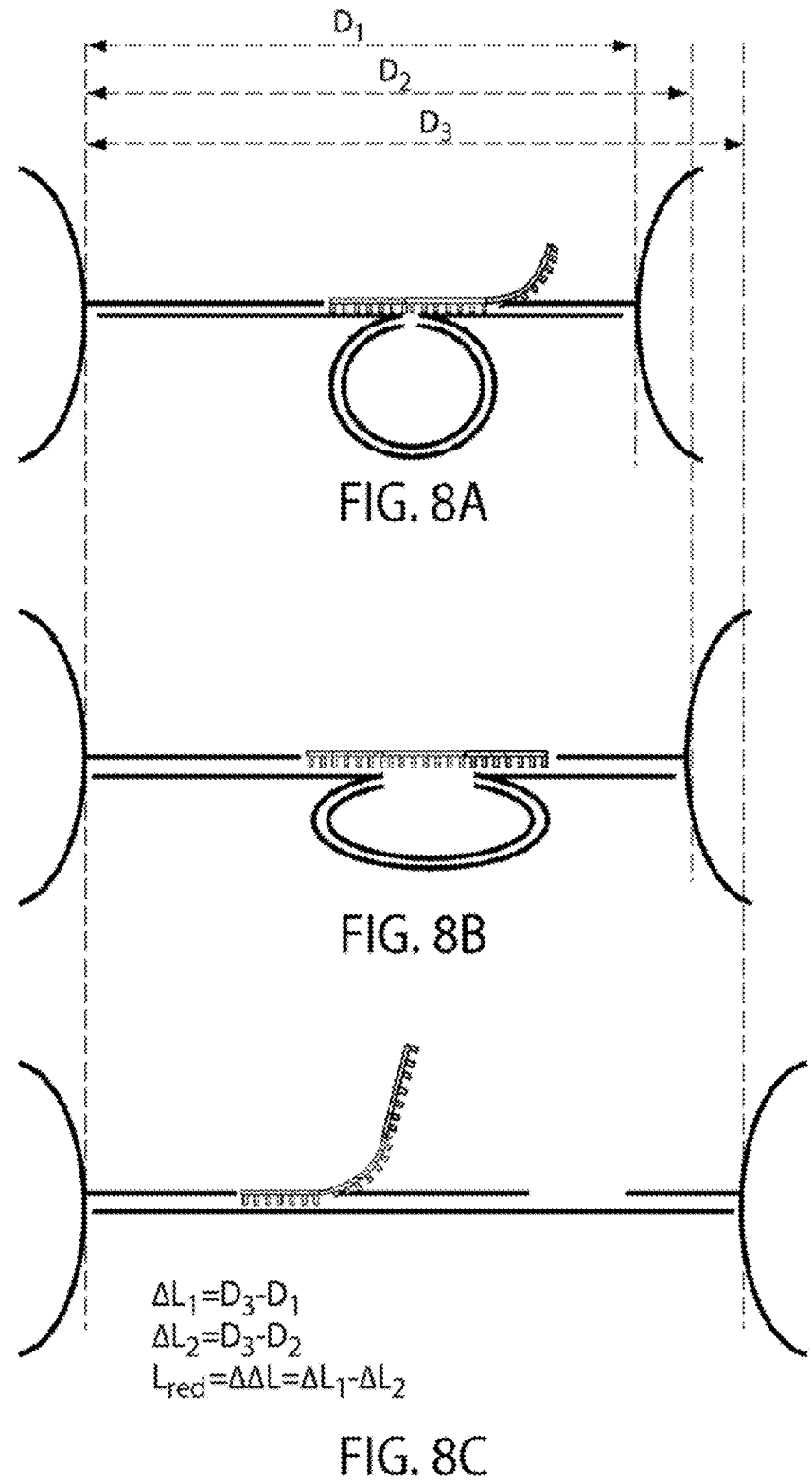

US 9,897,597 B2

HIGH-THROUGHPUT STRUCTURE DETERMINATION USING NUCLEIC ACID CALIPERS

RELATED APPLICATIONS

This application is a national stage filing under 35 U.S.C. § 371 of International Application No. PCT/US2015/027290, filed Apr. 23, 2015, which was published under PCT Article 21(2) in English, and which claims the benefit of U.S. Provisional Application No. 61/982,914 filed on Apr. 23, 2014, the entire contents of each of which are incorporated by reference herein.

FIELD OF INVENTION

The invention relates to and provides compositions, devices and methods for measuring intermolecular and intramolecular distances on a single-molecule basis.

BACKGROUND OF INVENTION

X-ray crystallography and solution NMR are mature fields that provide powerful tools for macromolecular structure determination. Nonetheless, structural characterization still poses a formidable challenge for many targets. For example, the diverse conformational transitions explored by unsynchronized populations of multi-protein complexes can confound bulk analytical approaches. CryoEM has the advantage of single-molecule imaging; however computational averaging is required for recovery of high-resolution structure. For samples exhibiting conformational heterogeneity, poor signal-to-noise under low-dose imaging leads to errors during class assignment of particles, thereby compromising effective resolution of reconstructions. Therefore a great need persists for novel technologies that can complement standard structural-biology approaches. A valuable source of such additional data is the long-range distance restraint, as sets of these considerably simplify the conformational search space for computational methods of structure determination. In the short term, long-range distance restraints can be used to refine models of docking of well-defined subunits, derived from previously determined x-ray or NMR studies, into larger complexes. In the longer term, these data could be used as the major source of experimental restraints for guiding de novo computational fold prediction. Single-molecule FRET is a promising approach for producing long-range distance restraints, however it currently requires extensive cysteine engineering along with complex instrumentation and analysis to obtain even a modest number of these distances. Thus no current methods exist for low-cost, high-throughput collection of long-range distance restraints at a single-molecule level.

SUMMARY OF INVENTION

The invention provides, inter alia, methods for high-throughput structure determination of a target of interest including macromolecules, such as proteins, nucleic acids, or complexes of multiple proteins and/or nucleic acids. The methods involve measuring long-range distances between randomly selected points on the target of interest, for example via force spectroscopy, and then identifying the points of attachment via a second measurement. These methods provide far greater throughput and ease of implementation compared to prior art methods for measuring long-range distance restraints. These methods also enable characterization of structural intermediates, stabilized by tension, that otherwise would be fleeting and therefore practically unobservable. These methods may be used to determine the structure of targets of known primary sequence or they may be used to solve the structure of a newly designed or isolated target.

Thus, in one aspect, this disclosure provides a system comprising (1) a single-stranded nucleic acid caliper having a target domain, wherein the target domain comprises non-contiguous nucleotide sequences, TS1 and TS2, complementary to a target splint and non-contiguous nucleotide sequences, TT1 and TT2, each complementary to distinct single-stranded nucleic acid handles, TH1 and TH2, flanking a target, (2) a target splint that is a single-stranded oligonucleotide having partial sequence complementarity to the single-stranded nucleic acid caliper, wherein the reference and target splints bind to separate distinct sequences of the single-stranded nucleic acid caliper and a TS toehold sequence that remains single-stranded when the target splint is bound to the single-stranded nucleic acid caliper.

In another aspect, this disclosure provides a system comprising (1) a single-stranded nucleic acid caliper having a reference domain and a target domain,
wherein (a) the reference domain comprises non-contiguous nucleotide sequences, RS1 and RS2, complementary to a reference splint and non-contiguous nucleotide sequences, RR1 and RR2, each complementary to distinct single-stranded nucleic acid handles, RH1 and RH2, flanking a reference molecule, and (b) the target domain comprises non-contiguous nucleotide sequences, TS1 and TS2, complementary to a target splint and non-contiguous nucleotide sequences, TT1 and TT2, each complementary to distinct single-stranded nucleic acid handles, TH1 and TH2, flanking a target, (2) a reference splint that is a single stranded oligonucleotide having partial sequence complementarity to the single-stranded nucleic acid caliper and a RS toehold sequence that remains single-stranded when the reference splint is bound to the single-stranded nucleic acid caliper, (3) a target splint that is a single-stranded oligonucleotide having partial sequence complementarity to the single-stranded nucleic acid caliper, wherein the reference and target splints bind to separate distinct sequences of the single-stranded nucleic acid caliper and a TS toehold sequence that remains single-stranded when the target splint is bound to the single-stranded nucleic acid caliper, and (4) a reference molecule flanked by two single-stranded nucleic acid handles, RH1 and RH2.

In some embodiments, either of the foregoing systems further comprise a target flanked by two single-stranded nucleic acid handles, TH1 and TH2.

In some embodiments, the single-stranded nucleic acid caliper is conjugated to a bead at a first end. In some embodiments, the single-stranded nucleic acid caliper is conjugated to a bead at a first end and to a surface at a second end. In some embodiments, the bead is a microbead. In some embodiments, the bead is a magnetic bead. In some embodiments, single-stranded nucleic acid the caliper is attached to a fixed surface.

In some embodiments, the system further comprises a RS displacement strand that is complementary to the sequence of the RS toehold sequence.

In some embodiments, the system further comprises a TS displacement strand that is complementary to the sequence of the TS toehold sequence.

In some embodiments, the target is a protein. In some embodiments, the target is a protein of known primary amino acid sequence. In some embodiments, the target is a protein of unknown primary amino acid sequence. In some embodiments, the target is a protein bound to a binding partner.

In some embodiments, the single-stranded handles, TS1 and TS2, are attached to the target at unmodified surface lysines. In some embodiments, the single-stranded handles, TS1 and TS2, are attached to the target at mutant surface cysteines. In some embodiments, the single-stranded handles, TS1 and TS2, are attached to the target at unmodified surface tryptophans.

In some embodiments, the target is a nucleic acid nanostructure.

In some embodiments, the single-stranded handles, TS1 and TS2, each comprise a hairpin barcode sequence and a loop sequence, wherein the hairpin barcode sequence is identical between TS1 and TS2, and the loop sequence is of different length between TS1 and TS2.

In some embodiments, the single-stranded handles, TS1 and TS2, each comprise a barcode sequence. In some embodiments, the barcode sequence is accessible via strand displacement. In some embodiments, the barcode sequence is present in a nested loop. The barcode may be a linear barcode or a nested barcode.

In another aspect, this disclosure provides a plurality of any of the foregoing systems. In some embodiments, the reference molecule, the reference splint, the RS1, RS2, RH1, RH2, RR1, RR2, TS1, TS2, TT1, TT2, TH1, TH2, TS toehold and RS toehold are identical between species in the plurality.

In some embodiments, the single stranded nucleic acid calipers are attached to a surface at a first end and to a bead at a second end.

In some embodiments, the plurality of systems are present in a centrifuge force microscope. In some embodiments, the centrifuge force microscope is a reflection interference contrast centrifuge force microscope (RIC-CFM).

In some embodiments, the single stranded nucleic acid calipers each comprises a unique sequence that forms a unique length looped structure.

In another aspect, this disclosure provides a method comprising (a) measuring, under tension, a bead-to-surface distance of any of the foregoing nucleic acid calipers attached to a surface on a first end and to a bead on a second end, when bound to a target flanked by single-stranded nucleic acid handles, and a target splint (BSD-background), (b) removing the target splint from the nucleic acid caliper, (c) measuring, under tension, the bead-to-surface distance of the nucleic acid caliper, when bound to a target flanked by single-stranded nucleic acid handles, but not bound to a target splint (BSD-target), and (d) determining the difference between BSD-target and BSD-background as a measure of the distance between points of attachment of the single stranded nucleic acid handles bound to the target when the target is in its native (non-denatured) conformation.

In another aspect, this disclosure provides a method comprising (a) measuring, under tension, a bead-to-surface distance of any of the foregoing nucleic acid calipers attached to a surface on a first end and to a bead on a second end, when bound to a reference molecule, a target flanked by single-stranded nucleic acid handles, and a target splint but not bound to a reference splint (BSD-ref), (b) removing the target splint from the nucleic acid caliper and hybridizing the reference splint to the nucleic acid caliper, (c) measuring, under tension, the bead-to-surface distance of the nucleic acid caliper, when bound to a reference molecule, a target flanked by single-stranded nucleic acid handles, a reference splint but not bound to a target splint (BSD-target), and (d) determining the difference between BSD-target and BSD-ref as a measure of the distance between points of attachment of the single stranded nucleic acid handles bound to the target when the target is in its native (non-denatured) conformation.

In some embodiments, the method further comprises measuring, under tension and denaturing conditions, the bead-to-surface distance of the nucleic acid caliper, when bound to the target, optionally to the reference and the reference splint if the caliper contains a reference domain, to obtain the distance between points of attachment of the single stranded nucleic acid handles bound to the target when the target is in its denatured conformation.

In some embodiments, the target is a protein. In some embodiments, the target is a protein of known primary amino acid sequence. In some embodiments, the target is a protein of unknown primary amino acid sequence. In some embodiments, the target is a nucleic acid nanostructure.

In some embodiments, the method further comprises measuring, under tension and in the presence of a first displacement nucleic acid, the bead-to-surface distance of the nucleic acid caliper, when bound to the target, optionally the reference and the reference splint if the nucleic acid caliper contains a reference domain, and the first displacement nucleic acid, to identify a first point of attachment of the single stranded nucleic acid handles to the target.

In some embodiments, the method further comprises measuring, under tension and in the presence of a second displacement nucleic acid, the bead-to-surface distance of the nucleic acid caliper, when bound to the target, optionally the reference and the reference splint if the caliper contains a reference domain, and the second displacement nucleic acid, to identify a second point of attachment of the single stranded nucleic acid handles to the target.

In some embodiments, tension comprises centrifugal force.

In some embodiments, the bead-to-surface distances is measured using centrifugal force microscopy incorporating reflection interference contrast. (RIC-CFM).

In some embodiments, under tension comprises under magnetic force. In some embodiments, under tension comprises under gravitational force.

In some embodiments, the handles are covalently attached to the target. In some embodiments, under tension means a force of about 300-1000 pN. In some embodiments, under tension means a force of less than about 10 pN.

In another aspect, this disclosure provides a method comprising (a) measuring, under tension, a bead-to-surface distance of a nucleic acid caliper attached to a surface at a first end and to a bead at a second end, when bound to an Xaa residue of a first unit and an Xaa residue of a second unit of a multi-unit target, wherein the Xaa residues of the first and second units are attached to single stranded nucleic acid handles of identical sequence, (b) attaching a second Yaa residue of the first unit to the nucleic acid caliper, and measuring, under tension and denaturing conditions, the bead-to-surface distance of the nucleic acid caliper when bound to the Xaa and Yaa residues of the first unit to identify the Xaa and Yaa residues on the first unit, and (c) dissociating the first unit from the nucleic acid caliper, attaching a second Yaa residue of the second unit to the nucleic acid caliper, and measuring, under tension and denaturing conditions, the bead-to-surface distance of the nucleic acid caliper when bound to the Xaa and Yaa residues of the second unit to identify the Xaa and Yaa residues on the second unit.

In some embodiments, the nucleic acid caliper comprises a reference domain and the measurements of (a), (b) and (c) are performed when the nucleic acid caliper is bound to a reference and a reference splint.

In some embodiments, the multi-unit target is a multi-unit protein. In some embodiments, the first and second units are proteins of known primary amino acid sequence. In some embodiments, the first and second units are proteins of unknown primary amino acid sequence.

In some embodiments, Xaa is lysine and Yaa is mutant cysteine.

In some embodiments, tension comprises centrifugal force. In some embodiments, the bead-to-surface distances are measured using centrifugal force microscopy incorporating reflection interference contrast. (RIC-CFM).

In some embodiments, tension comprises magnetic force. In some embodiments, tension comprises gravitational force. In some embodiments, the first unit is dissociated from the nucleic acid caliper using strand displacement.

In some embodiments, the denaturing conditions are presence of SDS.

In some embodiments, the handles are covalently attached to the target.

In another aspect, the disclosure provides a system comprising (1) a nucleic acid caliper having a looping domain, wherein the looping domain is flanked by sequences complementary to reference splint sequences RSS1 and RSS2, (2) a reference splint comprising a single stranded oligonucleotide having a first reference splint sequence RSS1 and a second reference splint sequence RSS2, and a target molecule attached at a first position to the reference splint between the RSS1 and RSS2 sequences and at a second position to a third reference splint sequence RSS3, wherein the second and third reference splint sequences, RSS1 and RSS3, are identical in sequence. The nucleic acid caliper forms two different looped states when hybridized to the first and second reference splint sequences (RSS1 and RSS2) and when hybridized to the first and third reference splint sequence (RSS1 and RSS3).

In some embodiments, the nucleic acid caliper is partially double stranded.

In some embodiments, the nucleic acid caliper is conjugated to a bead at a first end. In some embodiments, the nucleic acid caliper is conjugated to a bead at a first end and to a surface at a second end. In some embodiments, the bead is a microbead. In some embodiments, the bead is a magnetic bead. In some embodiments, the nucleic acid caliper is attached to a fixed surface.

In some embodiments, the target is a protein. In some embodiments, the target is a protein of known primary amino acid sequence. In some embodiments, the target is a protein of unknown primary amino acid sequence.

In some embodiments, the looped states are double stranded loop states. In some embodiments, the looped states can be regenerated once force is reduced or removed.

In another aspect, the disclosure provides a method comprising (a) measuring, under tension, a bead-to-surface distance (BSD-RS) of the foregoing nucleic acid caliper when attached to a surface on a first end and to a bead on a second end, when hybridized to a first reference splint sequence RSS1 and a second reference splint sequence RSS2 of a reference splint, (b) measuring, under tension, a bead-to-surface distance (BSD-target) of the nucleic acid caliper when hybridized to the first reference splint sequence RSS1 and a third reference splint sequence RSS3 of the reference splint, (c) measuring, under tension, a bead-to-surface distance of the nucleic acid caliper when hybridized to the first reference splint sequence RSS1 of the reference splint but not the second reference splint sequence RSS2 or the third reference splint sequence RSS3, and (d) determining the difference between BSD-target and BSD-RS as a measure of the length of the target.

In some embodiments, the target is a protein. In some embodiments, the target is a protein of known primary amino acid sequence. In some embodiments, the target is a protein of unknown primary amino acid sequence. In some embodiments, the target is a nucleic acid nanostructure.

In some embodiments, under tension means under centrifugal force.

In some embodiments, the bead-to-surface distances are measured using centrifugal force microscopy incorporating reflection interference contrast (RIC-CFM).

In some embodiments, under tension means under magnetic force. In some embodiments, under tension means under gravitational force.

In another aspect, the disclosure provides a method comprising (a) measuring, under tension, a bead-to-surface distance of a nucleic acid caliper attached to a surface at a first end and to a bead at a second end, when bound to an Xaa residue and a first Yaa residue of a target, wherein the Xaa and Yaa residues are attached to single stranded nucleic acid handles, (b) dissociating the nucleic acid caliper from the first Yaa residue and attaching the nucleic acid caliper to a second Yaa residue, (c) measuring, under tension, the bead-to-surface distance of the nucleic acid caliper when bound to the Xaa and second Yaa residues of the target, and (d) repeating steps (a)-(c).

In some embodiments, under tension means a force of about 300-1000 pN.

In some embodiments, the target is a protein.

In some embodiments, the method is carried out under denaturing conditions. In some embodiments, the denaturing conditions comprise the presence of SDS.

In some embodiments, the handles comprise barcode sequences. In some embodiments, the barcode sequences are accessible via strand displacement. In some embodiments, the barcode sequences are present are nested in a nucleic acid loop. The barcode may be a linear barcode or a nested barcode.

In some embodiments, the target is a protein of unknown primary amino acid sequence.

In some embodiments, Xaa is lysine and Yaa is mutant cysteine.

In some embodiments, under tension means under centrifugal force. In some embodiments, the bead-to-surface distances are measured using centrifugal force microscopy incorporating reflection interference contrast (RIC-CFM).

In some embodiments, under tension means under magnetic force. In some embodiments, under tension means under gravitational force.

In some embodiments, the first Yaa is dissociated from the nucleic acid caliper using strand displacement.

In some embodiments, steps (a) to (c) are performed multiple times at a force of less than about 10 pN, and then steps (a) to (c) are performed multiple times at a force of about 300-1000 pN.

In some embodiments, the handles are covalently attached to the target.

In some embodiments, the target is a macromolecular complex. In some embodiments, the macromolecular complex is a proteome. In some embodiments, the macromolecular complex is a transcriptome.

In some embodiments, the target is a polysaccharide and the residues are sugars.

In another aspect, the disclosure provides a method comprising
(a) providing a plurality of target nucleic acids, each comprising a template strand,
(b) performing a limited polymerase reaction on the plurality of target nucleic acids in the presence of deoxyuridine, thereby producing double stranded target nucleic acids having a template strand and a complementary strand comprising deoxyuridine,
(c) exposing the plurality of double stranded target nucleic acids to uracil DNA glycosylase to create 1 nucleotide gaps,
(d) exposing the plurality of double stranded target nucleic acids to exonuclease to widen the 1 nucleotide gaps,
(e) ligating barcoded, crosslinkable, end-protected oligonucleotides into the widened gaps,
(f) crosslinking the oligonucleotides to the template strands,
(g) contacting individual resultant barcoded target nucleic acids at a first and second barcoded position with a nucleic acid caliper,
(h) measuring the distance between, and identifying the barcodes at, the first and the second barcoded positions,
(i) releasing the caliper from the second barcoded position and reassociating the caliper with a third barcoded position, and
(j) repeating steps (g) to (i), each time maintaining attachment of the caliper to the target nucleic acid at one position, and attaching the caliper to the target nucleic acid at a new position.

In another aspect, the disclosure provides a method comprising
attaching a nucleic acid caliper comprising positions C1 and C2 to a target at positions X1 and Y1, whereby C1 attaches to X1 and C2 attaches to Y1,
measuring the distance between X1 and Y1, under tension and non-denaturing conditions,
releasing Y1 from C2, and optionally attaching or maintaining Y1 at another position on the caliper, C3,
attaching position C4 on the caliper to an additional position X2 on the target, and measuring the distance between X1 and X2 under tension and optionally under denaturing conditions, releasing C4 from X2, and repeating until sufficient primary sequence information for X1 is obtained, and
releasing X1 from C1,
attaching position C5 on the caliper to an additional position Y2 on the target, and measuring the distance between Y1 and Y2 under tension and optionally under denaturing conditions, releasing C5 from Y2, and repeating until sufficient primary sequence information for Y1 is obtained, wherein each position on the target has a unique barcode.

In some embodiments, C2 and C4 are identical positions. In some embodiments, C1 and C5 are identical positions.

In some embodiments, wherein the barcode is a linear or nested barcode.

In some embodiments, under tension and non-denaturing conditions comprises a force of less than 10 pN. In some embodiments, under tension and denaturing conditions comprises a force in the range of 300-1000 pN.

In some embodiments, the caliper is attached to a surface at a first end and to a bead at a second end.

In some embodiments, linkages within the caliper are covalent.

In some embodiments, positions on the target are labeled with single stranded nucleic acid handles. In some embodiments, the single stranded nucleic acid handles comprise unique barcodes.

In some embodiments, the target is a protein. In some embodiments, the target is a multi-component target.

The caliper may be any of the calipers described herein.

In embodiments of the various foregoing systems and calipers, linkages between various sequences and domains may be covalent.

These and other aspects and embodiments provided herein are described in greater detail herein.

BRIEF DESCRIPTION OF DRAWINGS

FIGS. 8A-D. Experimental design of a preliminary experiment performed in a dual-optical trap setup where two different parts of the splint are engaged separately to form a loop (A and B) that can be transitioned to an opened loop via force (C). (D) Histogram of loop length measurements from repeated measurements from a single tether. This setup has lower spatial resolution due to its image-based position tracking, as opposed to interference based measurements in RICM.

DETAILED DESCRIPTION OF INVENTION

The methods provides herein are used to determine structural features including complete 3D structure of targets of interest. Such targets include without limitation nucleic acid nanostructures, proteins, multiprotein complexes, protein-nucleic acid complexes, and the like. Any target that can be surface modified through attachment to nucleic acids, in a directed (i.e., non-random manner) can be analyzed according to the methods provided herein.

Certain methods provided herein stretch individual targets such as proteins and multi-protein complexes with nanoscale nucleic acid calipers, and measure the distances of such calipers upon stretching using high-throughput, high-resolution means such as but not limited to centrifugal force microscopy. Importantly, the methods can be performed on a single-molecule level and thus are not hindered by a bulk population analysis of certain existing methods.

The methods can be used to measure distances on targets that are stretched at varying levels of tension or that are manipulated in another manner, including for example association or dissociation with a binding partner. These methods can also be used to model the dynamics of large multi-component complexes from previously resolved subunit components, or in some instances can be used to predict a de novo structure.

These methods, which are described below in greater particularity, can be performed with only small amounts of sample (or target) with minimal preparation or modification of such sample or target. For example, in the context of protein structural determination, minimal or no cysteine engineering is necessary. Measurements at 2 Å spatial resolution can be collected on millions of target-loaded calipers per hour, each integrated over a period of 100 ms, or on thousands of target-loaded calipers per hour with millisecond temporal resolution.

Various methods provided herein may be performed using Centrifuge Force Microscopy (CFM) that incorporates Reflection Interference Contrast (RIC-CFM). RIC-CFM may be used to achieve parallel, high-resolution analysis of individual target-loaded nanocalipers each attached between a bead and a surface, thereby offering high throughput and ease of implementation. RIC-CFM is capable of achieving angstrom-spatial and millisecond-temporal resolutions.

Long-Range Distance Measurements Generally

Figure 1:
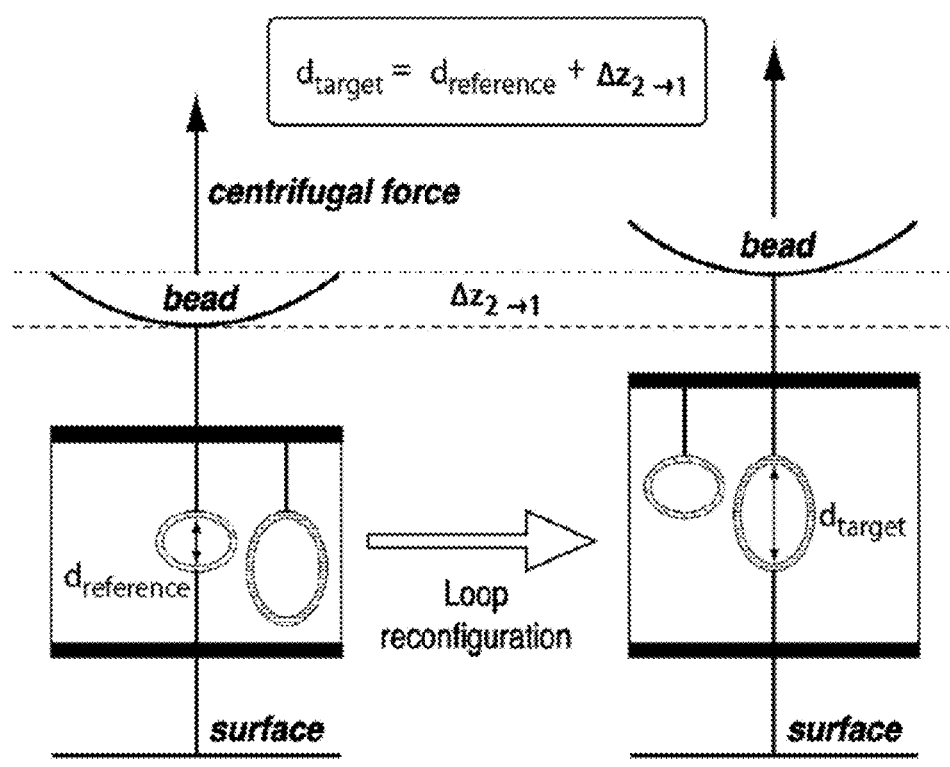
FIG. 1. Black-box schematic for caliper to measure long-range distance restraint.

The basic logic of the long-range distance measurement methods provided herein is shown in FIG. 1. Reference may also be made to FIGS. 2 and 7, which outline the method with more specificity.

A target, such as a target protein, nucleic acid, or complex, is fastened at two of its surface residues to a nucleic acid, sometimes referred to herein as a caliper or nanocaliper. The nucleic acid is itself attached at one end to a surface and at the other end to a bead such as a microbead. The bead may be moved away from the surface using centrifugal force (or in the case of a magnetic bead, using magnetic force). The bead may be moved away from the surface using gravitational force. The bead-to-surface distance is measured at various times during the method and it is the change in such distance that is used to determine the distance between the two points of attachment on the target, and thus the structure of the target.

In certain embodiments, the bead-to-surface distance (BSD) is measured relative to a reference state, as described now. The reference state is a state in which a mounted calibration reference determines the BSD versus a state where a mounted target determines the BSD. This difference measurement can be used to infer the distance between the two attachment points on the target.

The disclosure contemplates a scenario where both attachment points are known. For example, the attachment points may be two particular residues, the positions of which in the primary structure of a protein are known.

The disclosure also contemplates a scenario where the attachments are made at residues of a known type but unknown position. For example, the attachment points may be two lysines (due to the attachment chemistry used) but the positions of these lysines in the primary amino acid sequence of the target protein are unknown. In other words, in some instances, the attachment points will be lysines but which particular lysines in the target protein will not be known.

In these latter situations, an additional BSD will be measured for the target extended to its contour length under denaturing conditions. This distance will depend on the number of intervening residues in the primary sequence, and therefore can be used to deduce identity (i.e., position within the primary amino acid sequence, in the context of a target protein) for the pair of attachments. Importantly, this denaturation-driven identification of attachment points drastically reduces the need for site-specific tagging of target proteins.

As will be discussed herein, the second scenario can also be applied to determining the position and distance of single stranded (ss) nucleic acid "handles" on nucleic acid nanostructures.

As will also be discussed in greater detail herein, the method can also be extended to multi-protein complexes, where the individual subunits in the complex can be expressed as single-cysteine mutants, each tagged with two distinct single-stranded nucleic acid "handles", and then reconstituted into the intact multicomponent assembly. This allows the distance between residues on different subunits of a complex to be determined.

High-Throughput Structural Analysis of Single Unit Targets

Targets to be analyzed are modified at specific sites through the attachment of single-stranded nucleic acid handles (which may be referred to herein as ssDNA "handles", for brevity and as an example). The sites may be a subset of sites on the surface of the target (e.g., all surface lysines).

The method is used to measure the distance between these short ssDNA "handles" attached to two sites on a target protein. The handles may be attached to the target protein using a variety of chemistries, each of which has amino acid specificity. As an example, two randomly selected lysines on the surface of a target protein react with NHS-functionalized oligonucleotides, to form a target protein having two ssDNA handles attached to random lysines that are surface accessible. Similarly other chemistries can be used to attach to other surface residues. For example, thiol-specific reagents can be used to attach to cysteines, amine-specific reagents can be used to attach to an amino-terminus of a protein or to lysines), carboxyl-specific reagents can be used to attach to a carboxy-terminus of a protein or to aspartates or glutamates, guanidine-specific reagents can be used to attach to arginines, imidazole-specific reagents can be used to attach to histidines, phenol-specific reagents can be used to attach to tyrosines, indole-specific reagents can be used to attach to tryptophans, amino-terminus specific reagents can be used to attach to the amino terminus of a protein, and carboxy-terminus specific reagents can be used to attach to the carboxy terminus. Basle et al., Chemistry & Biology, 17:213 describes such various chemistries, and is incorporated by reference herein.

The first measurement is the distance between the two handles which is representative of the distance between the two surface residues. The second measurement is the distance between the two handles under denaturing conditions. This latter measurement identifies the position of those residues in the primary amino acid sequence of the target protein.

Figure 2A:
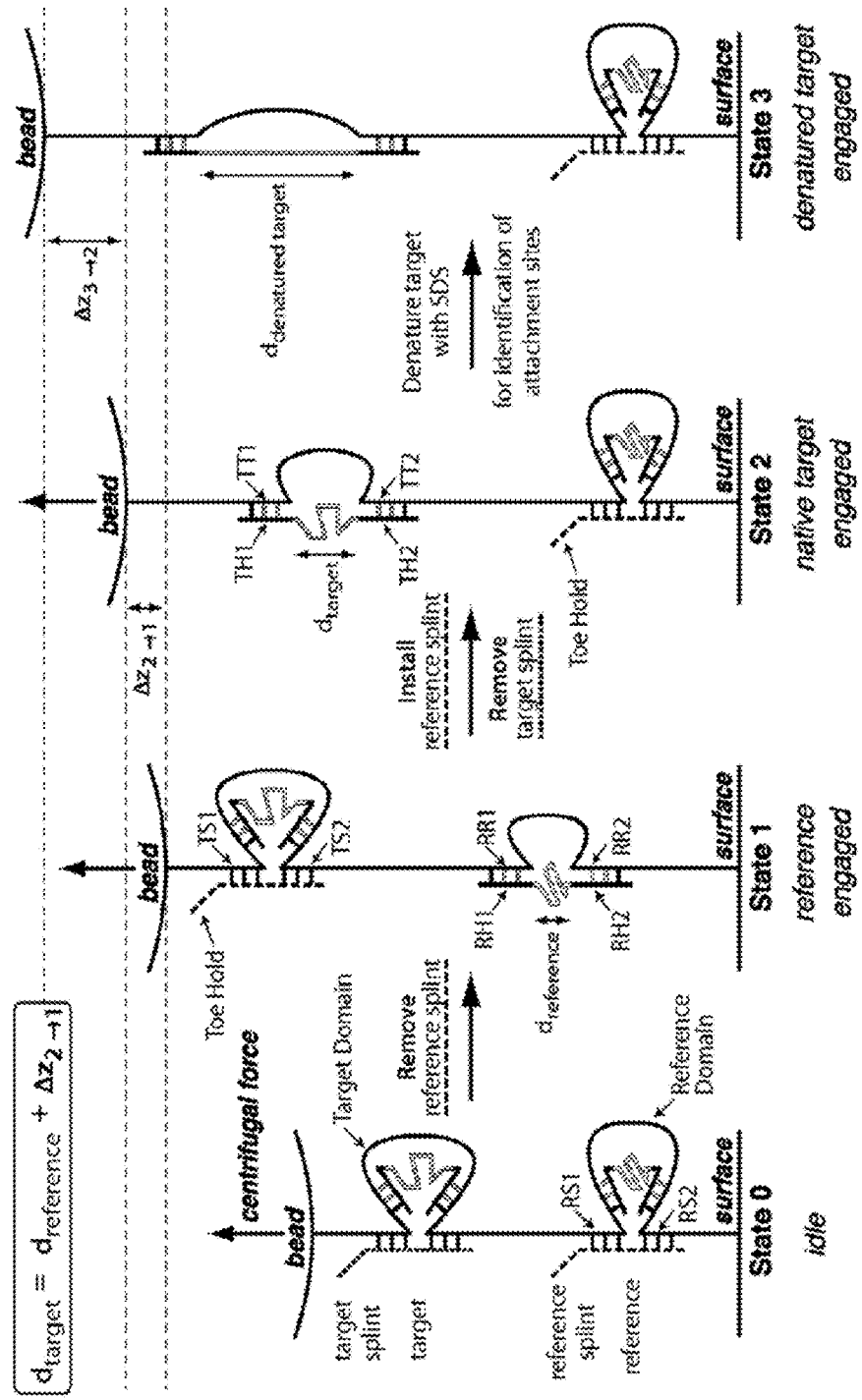
FIG. 2A. DNA-based nanocaliper CLP-I. Removal of a splint strand is achieved by microfluidic introduction of strands that are fully complementary to that splint strand. Complementary oligonucleotides (not shown) can be annealed to the exposed regions of the ssDNA backbone if necessary, in order to minimize unwanted secondary structure.

An example of a nanocaliper, referred to as CLP-I, is shown in FIG. 2A. This nanocaliper consists of a long ssDNA mounted between a surface and a bead that is stretched taut by an external force (e.g., optical trap or centrifugal force pulling at 5-30 pN). The strand is organized into two independent domains (a "target" (red) domain and a "reference" (green) domain), each consisting of a nested loop. The neck of each inner loop is bridged by a guest molecule. The target inner loop is bound to the target. The reference inner loop is bound to a calibration standard of known length (such as but not limited to dsDNA). The ssDNA handles and nanocalipers are designed to have complementary sequences thereby enabling the binding of the target at a particular region of the nanocaliper and the resultant loop formation. A target splint is also designed to have complementary sequence to the nanocaliper. The target splint may function to facilitate the binding of the target to the nanocaliper and/or to stabilize the target-loaded nanocaliper. The target splint can be removed, for example through a process of strand displacement, in order to measure distances in the target.

In some instances, the nanocaliper comprises a reference region, as illustrated in FIG. 2A. In other instances, the nanocaliper does not comprise a reference region.

When a nanocaliper with a reference region is used, a reference molecule similarly will have ssDNA handles. These handles and the nanocaliper will also be designed to have complementary sequences thereby enabling the binding of a reference molecule at a particular region of the nanocaliper and the resultant loop formation. A reference splint designed to have a complementary sequence to the nanocaliper may also be used. The reference splint may function to facilitate the binding of the reference molecule to the nanocaliper and/or to stabilize the reference-loaded nanocaliper. The reference splint can be removed, for example through a process of strand displacement, in order to measure distances in the reference, thereby calibrating the nanocaliper.

Thus, for each target, there will be a system comprising the caliper, the single stranded oligonucleotides to be attached to the target (and having complementary sequence to the caliper), and the single-stranded oligonucleotide to be used as the target splint. Additionally, the system may further comprise single stranded oligonucleotides to be attached to (or part of) the reference (and having complementary sequence to the caliper), and the single-stranded oligonucleotide to be used as the reference splint. Additionally, the system may further comprise the reference molecule itself. The system may also comprise the single stranded oligonucleotides used to displace the target splint and the reference splint. The nucleotide sequences of target and reference splints will be different, and accordingly the nucleotide sequences of the oligonucleotides used to displace the target and reference splints also will be different. Similarly, the nucleotide sequences of the target ssDNA handles will be different from the reference ssDNA handles. As will be readily apparent from FIG. 2A, each splint binds to non-contiguous sequences on the caliper, thereby forming a loop. Similarly, each target and reference binds to non-contiguous sequences on the caliper, thereby forming a loop.

It is to be understood that for brevity, the term ssDNA is used in this disclosure in a non-limiting manner and is intended to represent a single-stranded nucleic acid generally, including but not limited to single-stranded DNA. Similarly, the term nanocaliper is used in this disclosure in a non-limiting manner and is intended to represent a single-stranded nucleic acid of sufficient length to function as described herein. The terms caliper and nanocaliper are used interchangeably.

When the splint strand is present, the domain is in "idle". This is shown as "State 0" in FIG. 2A. The BSD represents the length of the caliper itself without interference from guest molecules (i.e., the length of the attached guest does not affect the length of the domain or of the entire caliper).

When the reference splint is removed (e.g., through strand displacement), the change in BSD represents the distance between the ssDNA handles on the reference molecule. This is shown as "State 1" in FIG. 2A. Typically, the reference molecule will be known as will be the distance between its attached ssDNA. The reference molecule may be a protein and it may in some instances be stretched to its contour length. Once the BSD in measured in the absence of the reference splint, the reference splint may be reintroduced and re-hybridized to the caliper, thereby reforming the reference loop.

The target splint is then removed (e.g., through strand displacement), and the BSD is measured again. This is shown as "State 2" in FIG. 2A. The difference in BSD can be measured between State 2, where only the outer loop of the target (red) domain is released, and State 1, where only the outer loop of the reference (green) domain is released. This difference is referred to herein as $\Delta z_{2 \to 1}$. Then the distance $d_{target}$, representing the unknown distance between handles on the target in its non-denatured form, can be recovered as shown in FIG. 2A, as a measured offset from the already known distance $d_{reference}$.

Thus, upon mixing with calipers, two of the handle-functionalized lysines will be randomly selected from each target for docking on a caliper. Then after $\Delta z_{2 \to 1}$ has been recorded, the target may be subjected to denaturing conditions in order to form State 3, as shown in FIG. 2A. Denaturing conditions will depend on the nature of the target. Protein denaturation can be performed in the presence of SDS, for example. The difference in BSD between State 3 and State 2, referred to as $\Delta z_{3 \to 2}$, then can be measured. This represents the extension of the target to its contour length following denaturation. The number of residues apart, n, in the primary amino acid sequence, in the case of a target protein, therefore can be inferred as $$n = ([d_{reference} + \Delta z_{2 \to 1} + \Delta z_{3 \to 2}] - 2d_{lysine\ side\ chain})/d_{c\alpha-c\alpha}$$

where $d_{c\alpha-c\alpha}$ is the distance between adjacent alpha-carbons in an extended polypeptide chain at the applied external force. This number, n, of intervening residues either will uniquely identify the lysine pair, or at a minimum will greatly constrain the possible pairings.

As will be understood based on this disclosure, for monomeric targets such as monomeric proteins, cysteine engineering of the target is not required. However, an intermediate handle-tagging approach could be used that involves the generation of targets having single cysteine mutants, and then attachment of one maleimide-ssDNA handle (specific for the cysteine mutant) and one NHS-ssDNA handle (specific for lysine) to each of those targets. Native cysteines will not have to be removed, as determination of n can be used to infer which cysteine-lysine pair has been tagged with ssDNA handles.

Any other chemically labile positions on the target (e.g., amino terminus or tyrosines, for example, in the context of a target protein) can be used as attachment points for the ssDNA handles. Reference can be made to Baslé et al., Protein chemical modification on endogenous amino acids. Chem Biol. 17, 213-227, 2010 for reactive moieties or groups that may be used to target various residues in a target protein.

High-Throughput Structural Analysis of Nucleic Acid Nanostructures

Nucleic acid nanostructure-based devices show promise for numerous applications (Pinheiro et al., Nat. Nanotechnol. 6:763-772, 2011). The methods of this disclosure can be used to determine the atomic-resolution structure of nucleic acid nanostructures. Similar to the afore-mentioned aspects, this aspect of the disclosure provides a high-throughput method for angstrom-resolution measurement of distances between pairs of nucleic acid (e.g., ssDNA) handles displayed on the surface of a nucleic acid nanostructure such as a DNA nanostructure formed using an origami synthesis approach. In this method, the two handles bind and loop out a segment of a long ssDNA that, in turn, is suspended between a surface and a bead such as a microbead pulled away by centrifugal (or magnetic or gravitational) force. The resting height of each bead reflects the distance between the handles, and the positions of millions of beads can be recovered per hour. These single bead (and thus single-nanostructure) measurements provide detail on static and dynamic heterogeneity of DNA nanostructures.

Figure 2B:
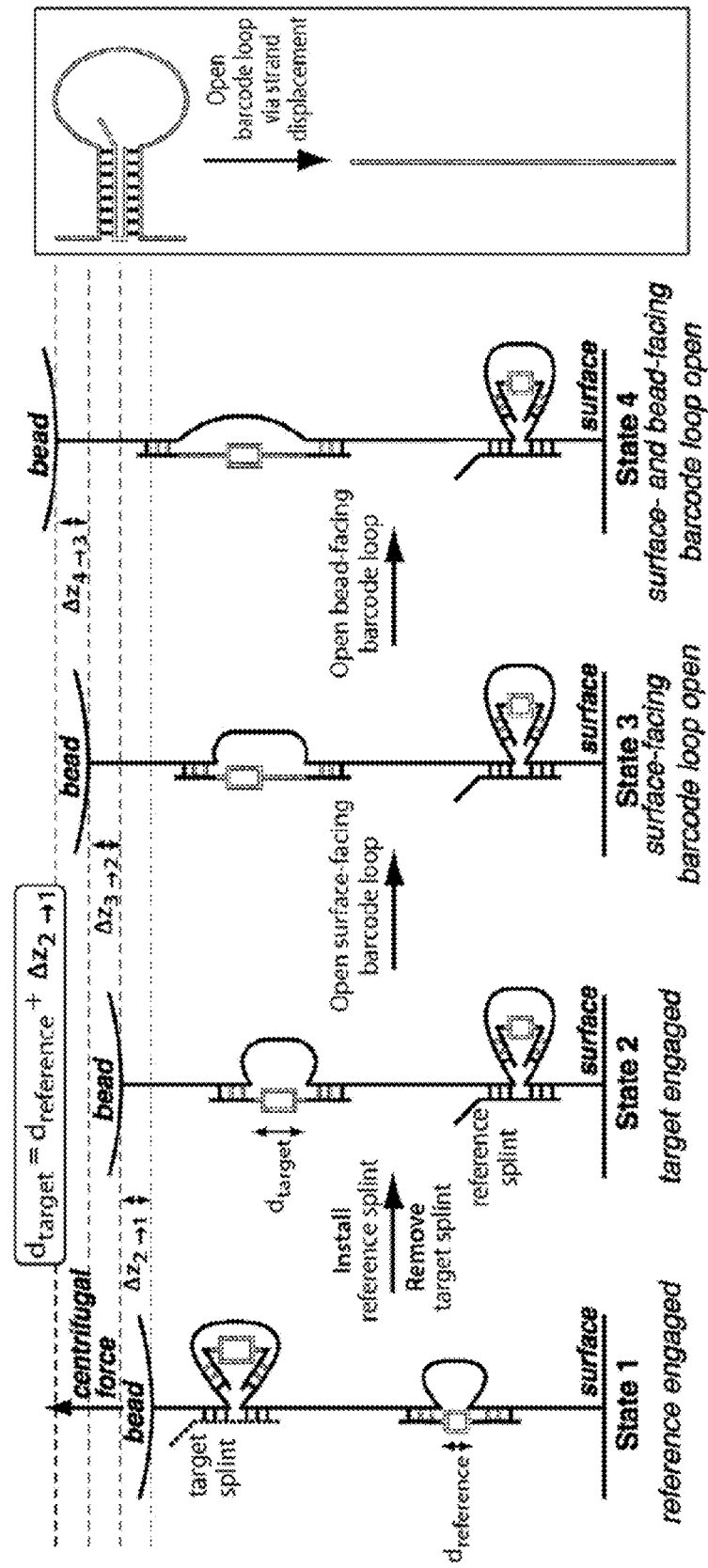
FIG. 2B. Structural determination of a nucleic acid nanostructure. Microfluidic introduction of strands actuates the assembly from one state to the next. In State 1, the reference (green) (e.g., dsDNA of known length) is engaged and determines the "reference" bead height. In State 2, the target (red) (e.g., DNA nanostructure) is engaged and determines the bead height. In State 3, a barcode-loop is opened on the surface-facing handle, allowing the bead to rise. In State 4, a barcode-loop is opened on the bead-facing handle. The exact amount of rise in bead height reveals the identity of the barcode. Right, structure of a barcode loop. Strand displacement leads to opening of loop. The same strand may be used to open all surface-facing handles. The same strand may be used to open all bead-facing handles. The strand used to open surface-facing handles will be different from the strand used to open bead-facing handles.

The method is used to measure the distance between two ssDNA handles displayed on the surface of a target nucleic acid nanostructure (NNS) (top or red rectangle in FIG. 2B). To enable this, the ssDNA handles will be hybridized to a single stranded nucleic acid (referred to herein as a caliper) such that a segment of the caliper is looped out, as shown in FIG. 2B. Then one end of the caliper is attached to a surface, and the other end to a bead such as a microbead. After a force is applied to stretch the bead away from the surface, the position of the bead can be determined and used to infer the distance between the two handles on the target. The method may be performed with or without calibration or reference. FIG. 2B illustrates a caliper comprising a target and a reference domain (similarly to FIG. 2A). The distance between the handles on the reference molecule is known. An example of such a reference is a dsDNA of defined length (bottom or green rectangle in FIG. 2B).

The disclosure contemplates that the target NNS is folded just a single time, with multiple surface-facing handles and multiple bead-facing handles displayed simultaneously. Then binding of an individual target to an individual caliper will select, at random, a single surface-facing handle and a single bead-facing handle. After the distance between these two handles is determined, the identity of the two handles (i.e., to which staple strand each is attached) can be discerned by reading out handle-embedded barcodes. Here each handle has a looped out "barcode" domain that can be released for example by strand displacement. The handles may be designed such that all surface-facing handles will be opened with the same strand, and similarly that all bead-facing handles will be opened with the strand. Thus, surface-facing handles will have an identical hairpin domain, but they will differ from each other in the length of the looped out sequence. Similarly, the bead-facing handles will have an identical hairpin domain, but they will differ from each other in the length of the looped out sequence. It is the length of the looped out sequence that "identifies" the handle. In FIG. 2B, the surface-facing handle is first opened (State 3) followed by the bead-facing handle (State 4). Upon triggered opening of the loop, the bead can rise to a new position to take up the released slack.

Figure 9A:
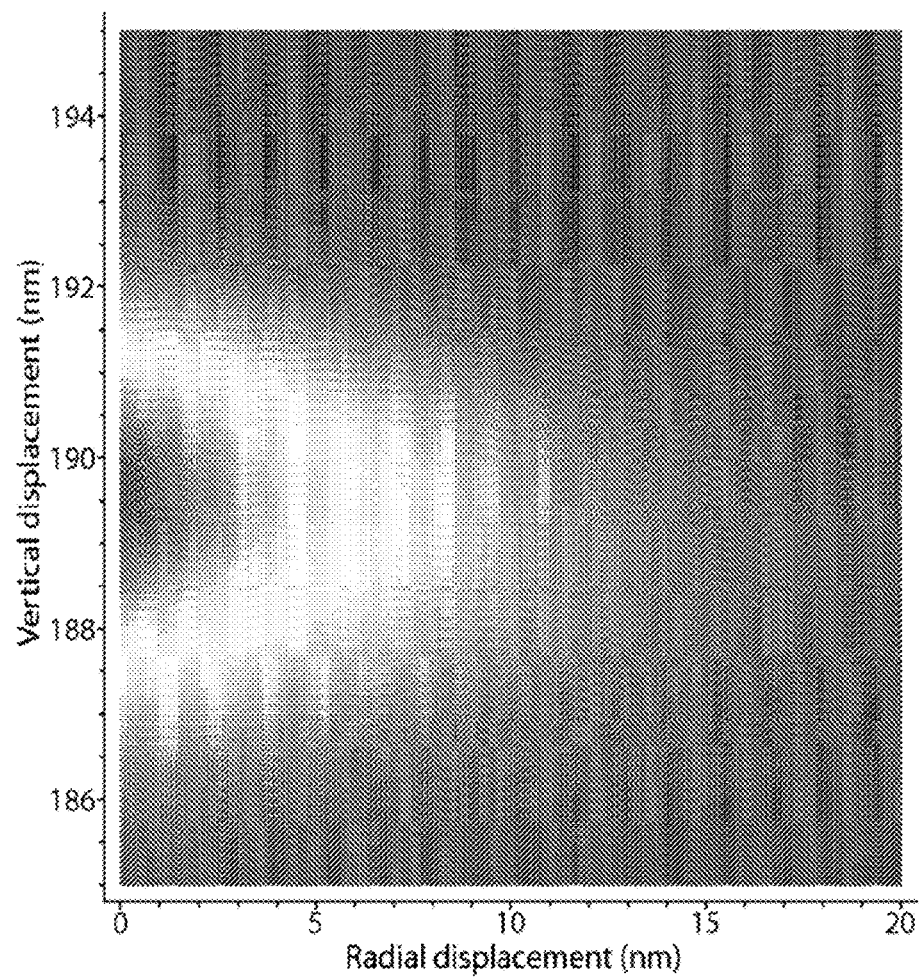
Figure 9B:
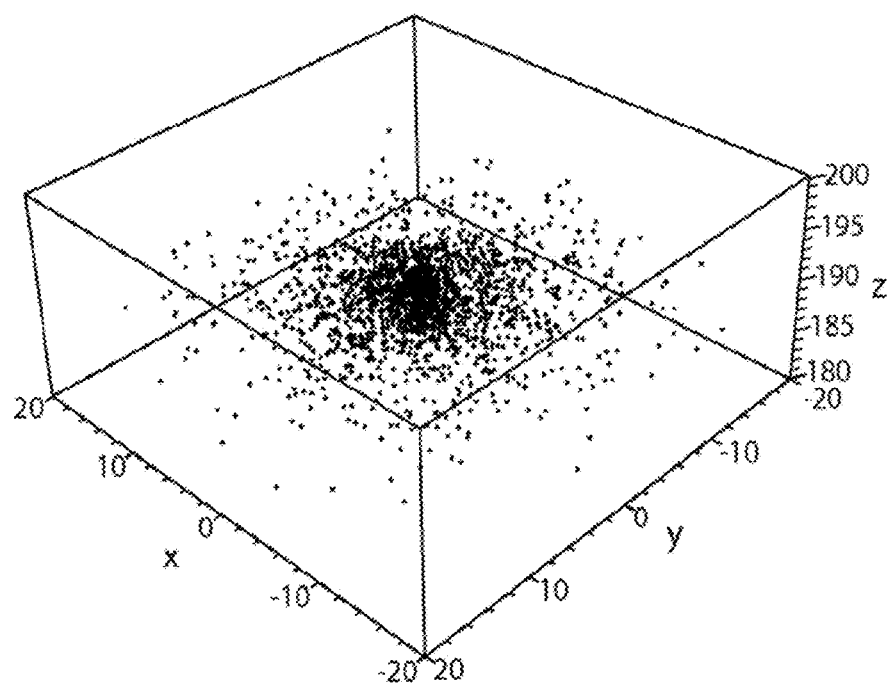

To estimate the performance of the system described in FIG. 2B, an experiment was conducted that simulated thermal noise distribution of a surface bound bead-tether system with a realistic polymer model for the tether and including both translational and rotational degrees of freedom of the bead. FIG. 9A for a typical positional distribution of the bead bottom due to thermal effects at room temperature for a dsDNA tether with a contour length of 200 nm, a bead radius of 1.5 μm and a force of 8 pN. The standard deviation of the height that would be measured from the RICM pattern is calculated to be 1.8 nm. FIG. 9B shows simulated data sampled from this distribution. With a 100 Hz frame rate and a 1 second observation time, it was possible to achieve a standard error of the mean of less than 2 angstroms. From previous studies, instrumental resolution is expected to be 1-2 angstroms (Wong et al. MRS Proceedings Vol 790 P5 1 (Cambridge Univ Press 2003). In addition, it is further contemplated to use previously developed imaging techniques that take advantage of image blur analysis to further improve localization (Wong and Halvorsen, Optics Express, 14: 12517-12531, 2006).

Figure 10:
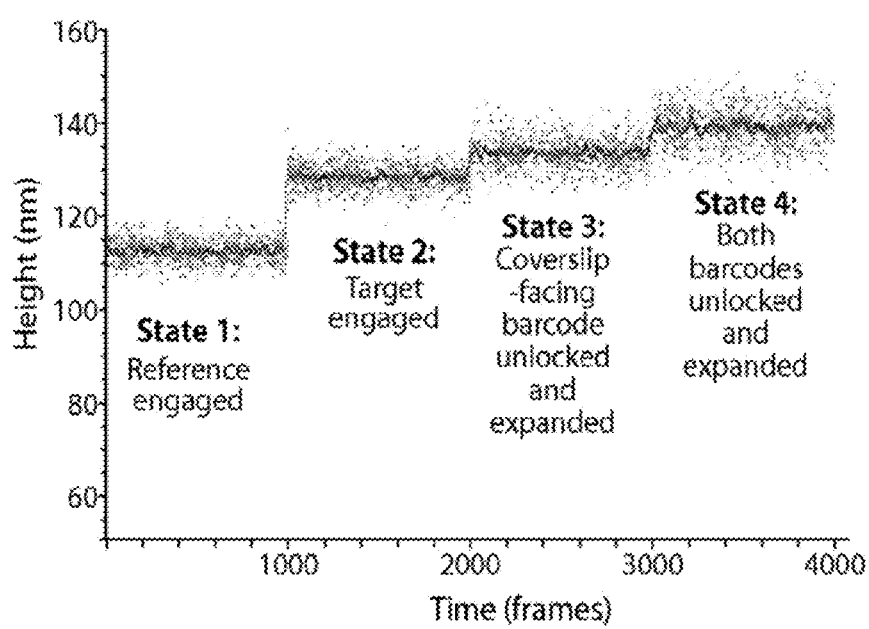
FIGS. 10A-B. (A) Calculated distribution for the bead bottom position in a setup where bead is tethered to a surface with a 200 nm dsDNA tether. (B) Simulated data for the same setup.

Using these calculations, a complete experiment as described in FIG. 2B was simulated. In FIG. 10B, a simulated set of time series data is illustrated (data: blue (scattered periphery dots), 20 frame moving average: orange (central dots)) which takes into account separate dsDNA, ssDNA, reference and target regions. These more detailed calculations also confirm angstrom-resolution capabilities of the design in FIG. 2B.

Long-Range Distance Measurements for Multi-Component Targets

Figure 3:
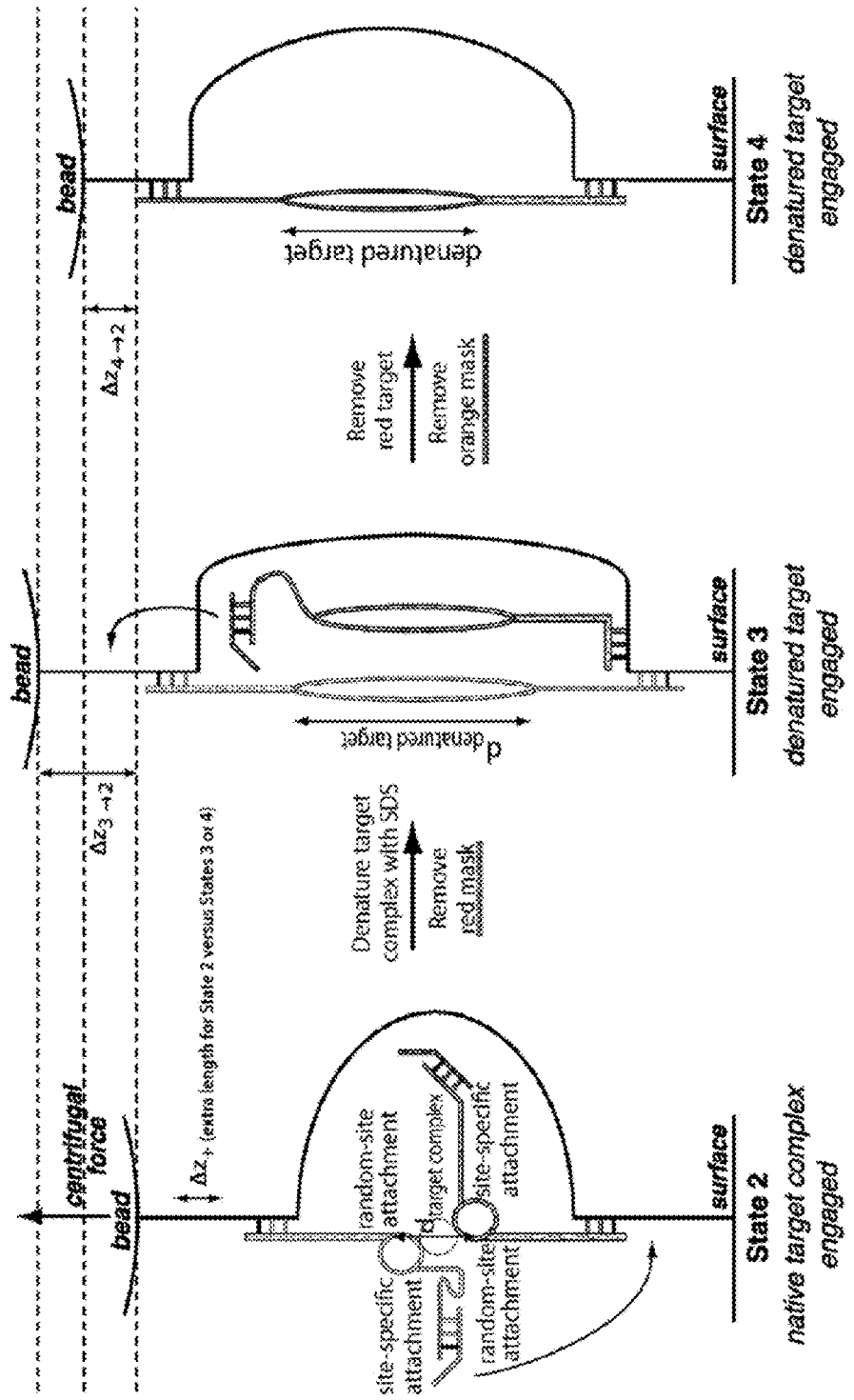
FIG. 3. Measuring target complex distance restraints and identifying attachment sites for multi-protein complexes using DNA-based nanocaliper CLP-II. Removal of a mask strand is achieved by microfluidic introduction of strands fully complementary to that mask strand. For brevity and clarity, the entire reference (green) domain as well as the outer loop for idling the target-complex domain, as in FIG. 2A, are omitted here but can be included in the actual device.

For multi-protein complexes, if two distinct subunits are attached to the caliper, then denaturation (e.g., with SDS) will break the connection between those two subunits. However, the denaturation method for identifying attachment residues still can be used in case the complex can be reconstituted from recombinant subunits, as outlined in FIG. 3. In this scenario, the complex consists of three subunits denoted red, grey, and orange. The red and orange subunits are expressed separately as mutants each with a unique cysteine (or any other unique reactivity, e.g., amino terminus). Then a "thin-red" maleimide handle is attached to the unique cysteine of the red subunit and a "thick-red" NHS-handle is attached to a random lysine of the red subunit. Likewise, a "thin-orange" maleimide handle and "thick-orange" NHS-handle are attached respectively to the unique cysteine and random lysine of the orange protein. All four handles have distinct sequences. Next, the functionalized red, gray, and functionalized orange subunits are reconstituted into the full complex and then docked on the nanocaliper, referred to as CLP-II, via the "thick-red" (red subunit lysine-attached) and "thick-orange" (orange subunit lysine-attached) handles to achieve State 2, as shown in FIG. 3.

Comparison of the bead z-position with a target complex engaged as described in the preceding paragraph (State 2) versus with a calibration reference engaged (State 1, omitted from FIG. 3 for brevity and clarity) can be used to recover the distance $d_{target\ complex}$ between the "thick-red" (red subunit lysine-attached) handle and the "thick-orange" (orange subunit lysine-attached) handle.

$$d_{target\ complex} = d_{reference} + \Delta z_{2 \to 1}$$

The next step is to identify the lysine residue attached to the "thick-red" (red subunit lysine-attached) handle. First, the complex is denatured (e.g., by SDS), and the "thin-red" (red subunit cysteine-attached) handle is demasked by strand displacement and subsequently docked to the nanocaliper below the site where the "thick-orange" (orange subunit lysine-attached) handle is bound to achieve State 3. Now the number of residues between the "thick-red" (red subunit lysine-attached) and "thin-red" (red subunit cysteine-attached) handles can be recovered as $$n_{red} = ([d_{target\ complex} + \Delta z_{3 \to 2} + \Delta z_+] - d_{lysine\ side\ chain} - d_{cysteine\ side\ chain})/d_{c\alpha\text{-}c\alpha}$$

where $\Delta z_+$ is a correction factor due to extra length present in State 2 compared to State 3 or State 4.

The final step is to identify the lysine residue attached to the "thick-orange" (orange subunit lysine-attached) handle. The "thin-orange" (orange subunit cysteine-attached) handle is demasked by strand displacement and docked to a position above the "thick-red" (red subunit lysine-attached) handle, and then the red target is removed completely by strand displacement to achieve State 4. Now the number of residues between the "thin-orange" (orange subunit cysteine-attached) and "thick-orange" (orange subunit lysine-attached) handles can be recovered as $$n_{orange} = ([d_{target\ complex} + \Delta z_{4 \to 2} + \Delta z_+] - d_{lysine\ side\ chain} - d_{cysteine\ side\ chain})/d_{c\alpha\text{-}c\alpha}$$

Force-Triggered DNA Calipers

Figures 7A, 7B, 7C:
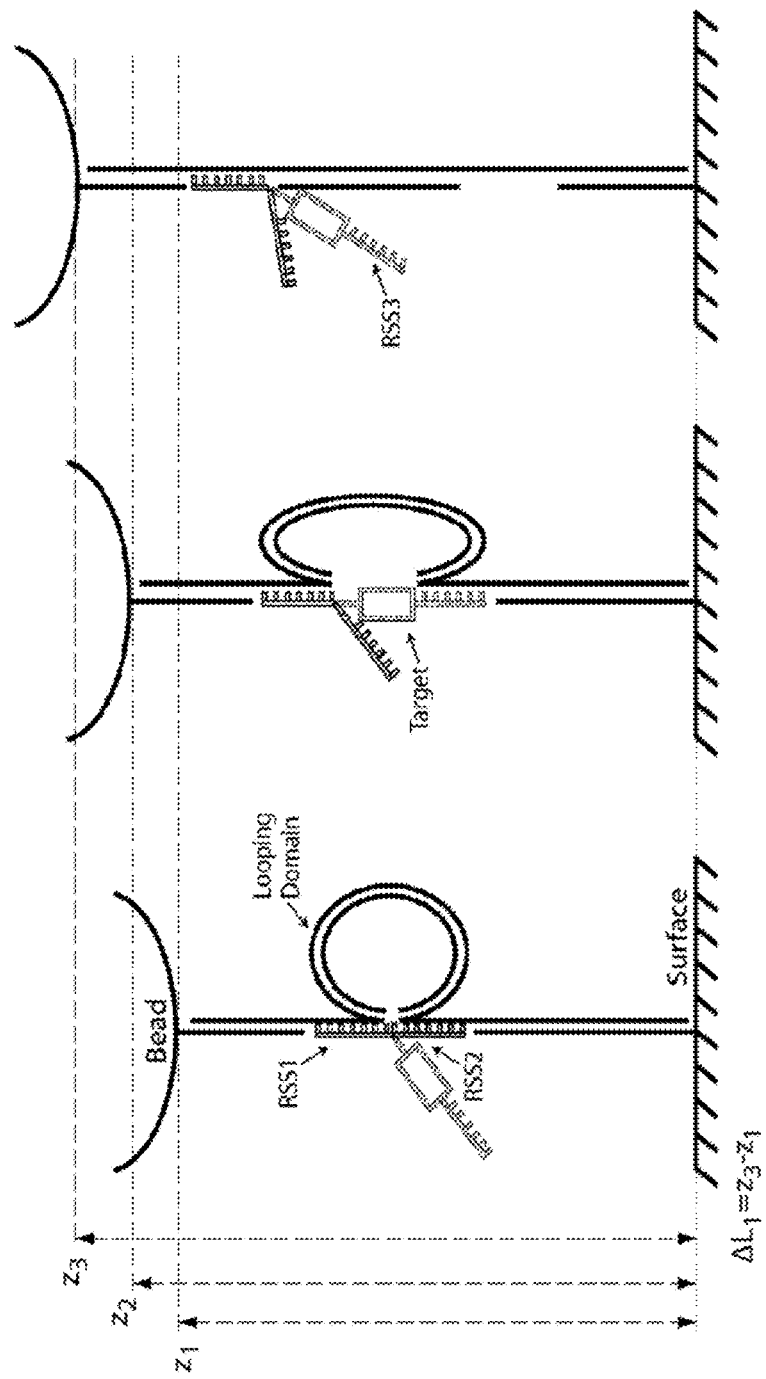
FIGS. 7A-C. Experimental design for a DNA caliper system. (A) A reference splint is engaged. (B) A target is engaged. (C) The loop is opened.

This disclosure further contemplates and provides another DNA caliper design that can be used to make macromolecular distance measurements using a force-triggered reconfigurable DNA tether. This embodiment does not require strand displacement to function, thus it allows DNA caliper measurements to be made with our existing single-molecule instruments without implementing an integrated fluid exchange system. One exemplification of this approach is illustrated in FIGS. 7A-C. Briefly, a DNA tether linking a bead to a surface can form two different possible looped states: one in which the target molecule (or target) is within the line of force, and one in which the target molecule is absent. By opening these two different loop states through the application of force, and comparing the change in length between these two states, the distance between the two attachment points on the target molecule can be determined.

In FIG. 7A-C, a resting upward force (~8 pN) is applied to the bead to stretch the DNA tether. There is a structure attached to the tether, consisting of an ssDNA splint in two distinct sequences (shown in blue-green) that latches two regions on the tether by complementary hybridization to form a loop. (This structure is shown in FIG. 7A as the two sequences hybridized to sequence that is upstream and downstream of the loop.) The target molecule (red rectangle) is attached to the internal point of the splint between the two sequences. Another point on the target molecule has an ssDNA handle (shown in red, and referred to herein as a target handle) that is identical in sequence to one side (shown in green) of the splint. The ssDNA handle bound to or part of the target molecule is shown in FIG. 7A extending from the rectangle, and thus not hybridized to the tether, and in FIG. 7B hybridized to the tether having displaced the strand now shown as extended and unhybridized. Measurements are made by carrying out the following steps:

Step 1: Bead-to-surface distance is measured when the tether is in a looped state ($z_1$ or $z_2$).

Step 2: By applying force, the loop is broken and bead to surface distance is measured again for the unlooped state ($z_3$).

Step 3: Difference between these two measurements is taken as a loop length measurement for this cycle ($\Delta L$, see equations in FIGS. 7A-C).

Step 4: Tether is relaxed and loop is reformed to repeat the cycle. Randomly either the target handle or one side of the splint will be attached.

Analysis: Two populations of loop length measurements ($\Delta L_1$ and $\Delta L_2$) are resolved and the distance between the mean values gives the length of the target (i.e., the length of the rectangle). Bead goes to height $z_3$ at every cycle, and this provides the end user the ability to check for drift between measurements.

A preliminary experiment that is a variant of the foregoing design was performed using a lower spatial resolution setup than the one illustrated in FIGS. 7A-C (i.e., using resolution lower than the resolution that can be achieved using RICM). The design of the experiment is provided in FIGS. 8A-C, and the data are provided in FIG. 8D. Briefly, a tether in the form of M13 DNA has been captured between two beads that are held by two optical traps. The tether was attached to the beads by a biotin-streptavidin interaction on one end and digoxigenin-anti-digoxigenin antibody interaction on the other end. The loop-forming ssDNA splint on the tether consists of three parts: a 40 base long anchor part that is complementary to a certain region on the tether (shown in cyan, left-most sequence) and two identical 20 base long parts complementary to a different region on the tether (shown in red and green, middle and right-most sequences). The rest of the tether was tiled with complementary pieces of DNA to remove any secondary structure (sequences 5' and 3' of the loop-forming splint).

The experiment was carried out as follows:

Step 1: Distance between the beads is measured when the tether is in a looped state (D1 or D2).

Step 2: By applying force (~50 pN), the 20 base pair side of the splint is sheared off to measure the full length of the tether (D3).

Step 3: The difference between these two measurements is taken as a loop length measurement for this cycle (ΔL, see equations in FIGS. 8A-C).

Step 4: Beads are moved closer to relax the tether, causing the loop to reform rapidly (~30 seconds) by hybridization of one of the 20 base long pieces.

Figure 8D:
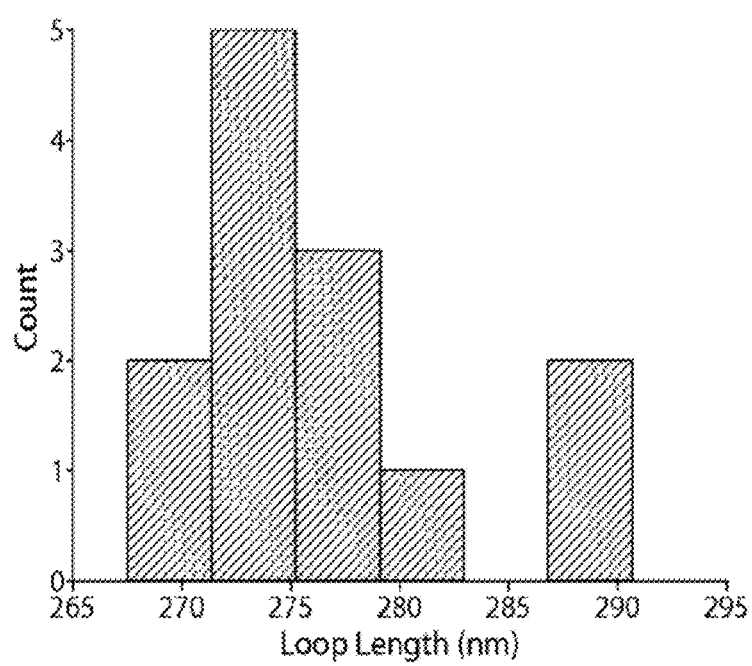

This cycle can be repeated multiple times (e.g., 10-20 times, or more) per tether or until a structural failure is observed, typically elsewhere, in the structure. Such structural failures may be avoided by using covalent attachments. FIG. 8D is a histogram of length measurements from one of these preliminary experiments. As can be seen even with this small number of measurements, it is possible to resolve two peaks that are about 15 nm apart, which is the expected length for a 20 base pair ssDNA molecule within the ~2 nm expected resolution of this particular dual-bead optical trap setup. This resolution may be increased by use of RICM, which system is described for example in published patent application US 20130288349. The results of this experiment also reveal steric effects within the particular structure used that result in more probable binding of one part over the other.

Barcodes

The nucleic acid systems described herein may be referred to as "DNA-Puppeteered Calipers" or DPC. The DPC may be used for a variety of applications. Prior to describing such applications, the following brief functional description of DPC is provided:

The operation of DPC involves cycling two primitive actions:

(1) reconfiguration (via strand displacement or other perturbation) to engage a new orientation of a target (or analyte) into the force-bearing path, and to disengage other targets (or analytes) into non-force-bearing paths or branches of each device, and (2) high-throughput, high-resolution sampling of the force-extension curve for the force-bearing path of each device.

DPC can be used to determine three kinds of information about biopolymers and their complexes:

(1) 1D sequence fingerprint, which is a set of pairwise distances within the primary sequence of a biopolymer chain for residues of defined sidechain types (e.g. lysine-to-lysine distances, cysteine-to-lysine distances);

(2) 3D surface fingerprint, which is a set of pairwise distances between residues on the surface of a native target, along with identification of the primary-sequence identity of each of those residues; and (3) barcode readout, which is a decoding of information embedded into ssDNA barcodes attached to the target analyte.

As will be described below, 3D surface fingerprinting is aided both by barcode readout as well as by 1D sequence fingerprinting.

Fingerprinting is mediated via labeling of targets at randomly sampled residues by ssDNA handles that serve as potential attachment points to a caliper. The ssDNA handles additionally can include DPC-decodable barcodes that digitally encode information such as the residue type to which it is attached (e.g., cysteine, lysine, etc.). Another important type of information is a randomly selected unique barcode that can be used for identifying handles previously sampled by the caliper (analogous to uniquely colored flags dropped at intersections while traversing a labyrinth). Other kinds of information could include the history of the target, such as what mutations it has in the case it was recombinantly produced (i.e., its relative genotype), what environmental conditions it has experienced (e.g., subjected to stress in the past), when and where it was tagged, etc.

A 1D sequence fingerprint can be determined by a two-legged molecular crawler (i.e., caliper) that randomly grabs two handles on a single chain, pulls with relatively high force (e.g., 300-1000 pN) to stretch that intervening segment to near its contour length, and then reports that length to enable inference of the distance in the primary sequence. The residue types (e.g. cysteine, lysine, etc.) can be read out by decoding barcodes embedded in the handles. The unique identifier barcode also can be read out at this time. Then the crawler releases one handle, and randomly grabs another handle on the same biopolymer chain, and the cycle repeats. In this way, a large number of primary-sequence correlations, equivalent to a partial sequence for the chain, can be obtained.

A 3D surface fingerprint can be determined by a two-legged molecular crawler (i.e., caliper) that randomly grabs two handles on a target, however this time it uses relatively low force (i.e., less than 10 pN, including for example about 8 pN) so that it doesn't denature the target. The unique identifier barcodes can be read out as well at this time. Then the crawler releases one handle, randomly grabs another handle on the same target, and the cycle repeats. In this way, a large number of pairwise distance measurements can be made for points sampling the surface of a single target. In the subsequent phase, the analysis is repeated on the same target at high force to determine the 1D sequence fingerprint of each component chain in the complex. Indexing of the identifier barcodes read out during the 1D fingerprinting phase allows assignment of the sequence identification of each handle grabbed during 3D surface fingerprinting. Note that the caliper only will be able to obtain a 1D sequence fingerprint on the chains that it does not release while operating under conditions that denature the constituent target chains. Therefore the caliper should have multiple arms to hold multiple chains so that many chains of a given target can be sequentially analyzed by 1D sequence fingerprinting.

Thus, as an example, a caliper described herein can be used to map targets such as multi-component targets using a two-step process. First, the caliper is allowed to attach itself randomly to a first position, X1, and a second position, Y1, on a target. The caliper binds to X1 and Y1 at C1 and C2 (i.e., C1 and C2 are positions or locations on the caliper). The distance between X1 and Y1 is measured, usually under non-denaturing conditions. Each of positions X1 and Y1 can be identified using barcodes such as linear or nested barcodes. The caliper disengages from Y1, while maintaining its attachment to X1. The caliper may completely or partially disengage from Y1. Partial disengagement means that the caliper releases Y1 from the C2 caliper position but the caliper does not release Y1 entirely, instead engaging Y1 at another caliper position C3. The caliper is then used to engage additional sites, in a sequential manner, starting with X1 or Y1. For example, the caliper maintains its attachment to X1 (through C1), and then binds additional positions X2, X3, X4, X5, etc, and the distances between X1 and each of these positions are measured. This provides information relating to the primary sequence around the X1 position. The caliper then binds additional positions with respect to the Y1 position (i.e., additional positions Y2, Y3, Y4, Y5, etc.) and the distances between Y1 and these additional positions are measured. This provides information relating to the primary sequence around the Y1 position. The initial measurement between X1 and Y1 may be performed under conditions that maintain the native state of the complex. The subsequent measurements between X1 and X2, X3, X4, X5, etc. and between Y1 and Y2, Y3, Y4, Y5, etc. may be performed under denaturing conditions (e.g., by flowing denaturant through the reaction chamber).

Figure 11:
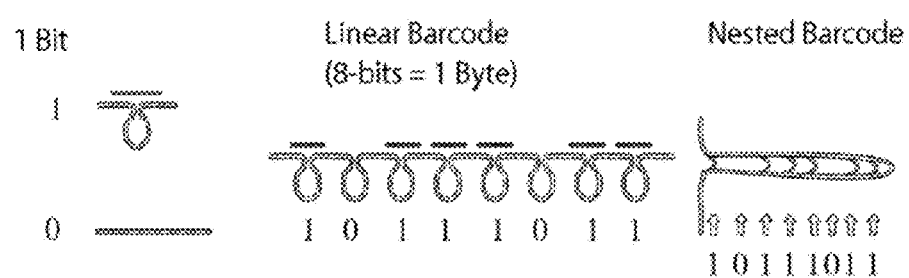
FIG. 11. Simulated time series data of the experimental setup outlined in FIG. 2B, for a reference length of 50 nm and a target length of 40 nm. Blue (periphery) dots are the simulated data and the orange (middle) dots are 20-frame running averages. The plateaus represent different states. From left to right (and from lowest to highest heights), they are as follows: State 1 representing the reference engaged; State 2 representing the target engaged; State 3 representing the coverslip-facing barcode unlocked and expanded; State 4 representing both barcodes unlocked and expanded.

Stepwise Elongation Barcodes: Here a barcode architecture is described that can be read out as a series of pre-programmed-length increases of a ssDNA strand, each actuated by fluidic introduction of a displacement strand. This is illustrated in FIG. 11. One architecture is a series of segments of a long scaffold strand each looped out by a staple strand. We will encode either a "0" or a "1" on each segment by fluidic introduction of staple strands that loop out either half the length or the entire length of the segment, respectively. For example, let the segment length be 100 nt. Then define a "1" staple strand that bridges two 20 nt subsegments, with a 60 nt end loop, and thereby reduces the end-to-end segment distance to 0 nt plus the span of the bridge. Then define a "0" staple strand that bridges another two 20 nt subsegments, with a 10 nt end loop, that is nested within the 60 nt end loop previously defined; this "0" staple strand (in the absence of the "1" staple strand) reduces the end-to-end segment distance to 50 nt plus the span of the bridge. Each staple strand has a unique sequence, therefore each loop can be independently opened by fluidic introduction of a displacement strand complementary to one half of the staple strand, and reclosed by removal of the displacement strand via fluidic introduction of a recovery strand that is complementary to the displacement strand.

For example, let there be n unique segments in series. Then there is a unique "0" staple strand and a unique "1" staple strand for each segment. To create a particular barcode, for each segment, select either the "0" or the "1" staple strand to include in the folding. Then there are $2^n$ potential barcodes. A barcode is read out by sequential introduction of displacement strands while observing changes in length. Anytime a staple-strand mediated bridge is disrupted, which only will be possible when that staple strand had been included on that barcode during its initial construction, then a length increase can be observed.

An simplified alternative design represents a "1" by the presence of a staple strand, and a "0" by its absence.

An alternative readout approach is to use force rather than strand displacement to trigger length changes within the barcode. Each bit (loop+staple strand) could be designed so that the staple strand breaks off at a specific force level with, for example, increasing levels of force required to go from the least significant bit to the most significant bit. The readout process could be made to be reversible by making each staple strand stronger on one-side than on the other, enable reannealing upon the reduction of force. One advantage of this design is that flow would not be required to readout the barcode, enabling this barcode to be used with standard single-molecule force probe instruments.

A second contemplated architecture comprises nested loops. This is also illustrated in FIG. 11 (right panel). As with the first design, the barcode can be read out as a series of length increases due to strand displacement. These nested loops can take the form of a large loop, with multiple staple strands closing the loop at different sizes. The presence or absence of each staple strand can encode a "1" or a "0". As with the first architecture, readout could either be accomplished using strand displacement to probe each bit in turn, or using force, unzipping the loop from the least significant bit to the most significant bit.

Unlike traditional DNA-based barcodes, the information is not stored directly in the sequence of the barcode, but rather in its geometry. Thus, DNA synthesis and sequencing are not required to write and read the barcode. Instead, hybridization is all that is required to write the barcode, and observing a change in geometry and length is all that is required to read the barcode.

Creating a Combinatorial Library of Stepwise Elongation Barcodes:

A library of barcodes may be created using a split and combine synthesis approach. First, scaffold strands are attached to beads. Then for each segment, the pool of beads is split into two, and the "0" staple strand is added to one subpool, and the "1" staple strand is added to the other subpool. Then excess staple strands are washed away from each subpool, and the subpools are combined together. The split and combine cycle are repeated for each segment.

Alternatively, for the design in which a "1" represents the presence of a staple strand, and a "0" represents its absence, a collection of barcodes could be generated stoichastically, by mixing the barcode with a collection of staple strands such that each barcode only binds to a subset of the staple strands. If enough unique combinations were made, this would be sufficient to uniquely identify each handle on a given macromolecule. It would be like a hashtag, with a small but not zero probability of two identically barcoded handles ending up on the same molecule (known as a "collision").

Imaging and Measurement Techniques

Figure 4:
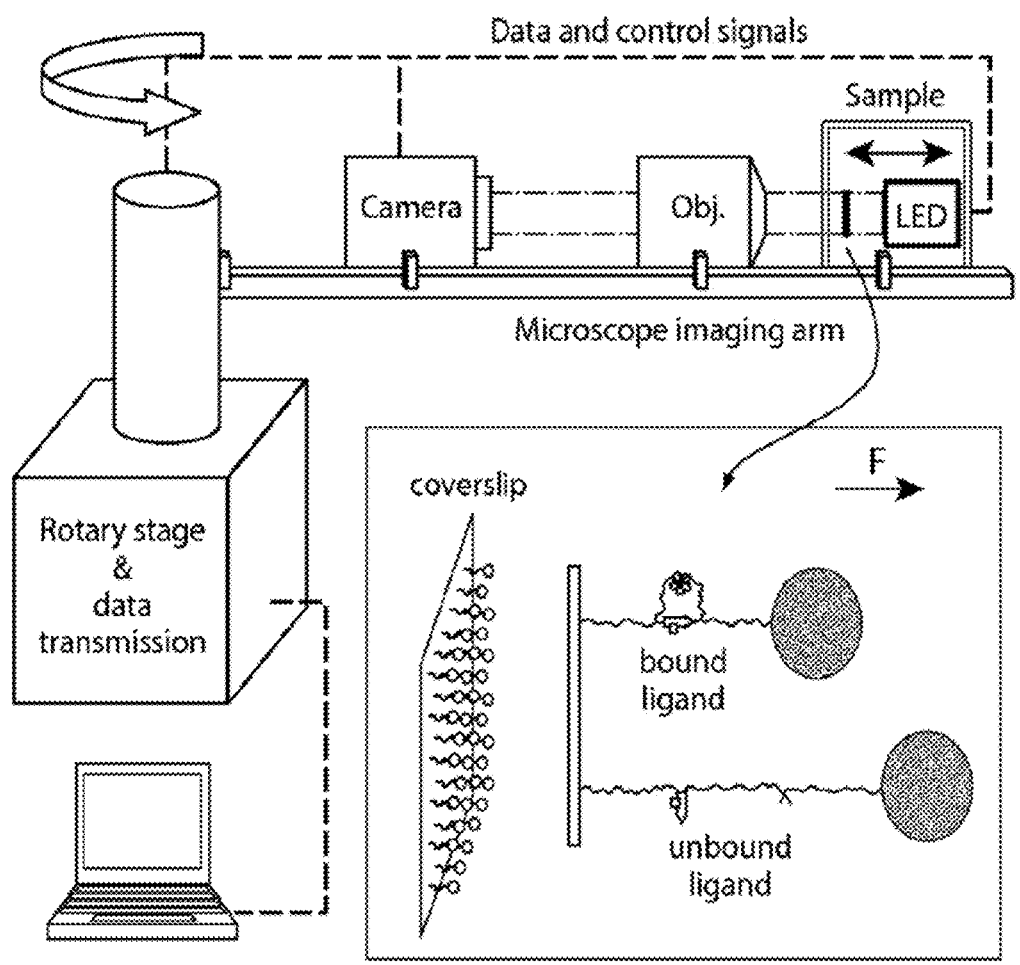
FIG. 4. Massively-parallel single-molecule measurements on the Centrifuge Force Microscope (CFM). Schematic of the CFM. A rotating microscope imaging arm enables the application of centrifugal force to a sample during observation. Force is applied to single-molecule complexes by pulling on functionalized beads tethered to the coverslip by single biomolecules.
Figure 5A:
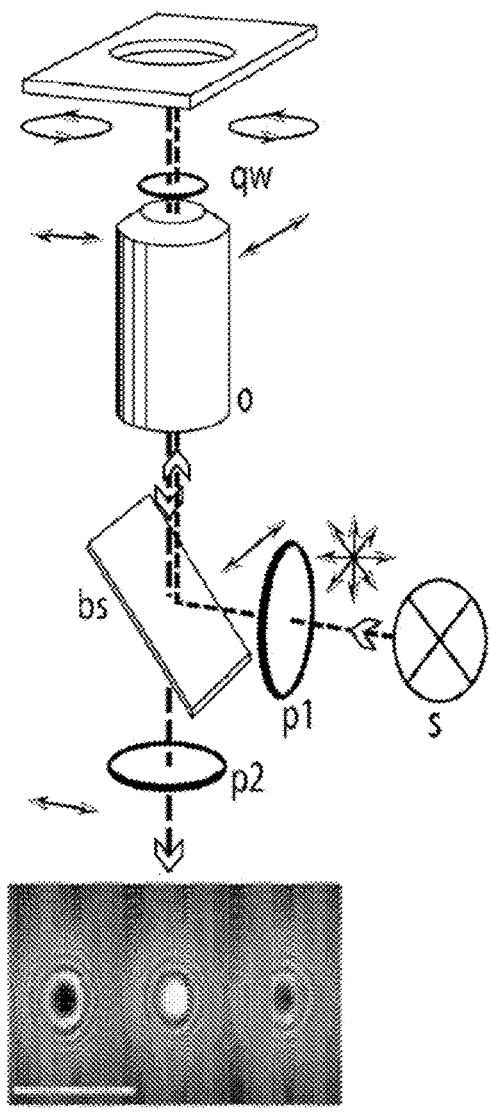
FIGS. 5A-D. Overview of 3D Reflection Interference Contrast Microscopy. (A) Schematic of the imaging light path with monochromatic source (s), polarizers (p1 and p2), beamsplitter (bs), objective (o), and quarter wave plate (qw). RICM patterns of a 7.5 μm bead at three different heights (10 μm scale bar) are shown at the bottom. (B) Simple model showing the principle of operation. (C) Example of a radial intensity profile from a microsphere and a fit with the model provided herein. (D) High-resolution 3D position map of a tethered bead with no force (below) and with applied tension from an optical trap at two laser powers (above) (Heinrich et. al., 2008).
Figure 5B:
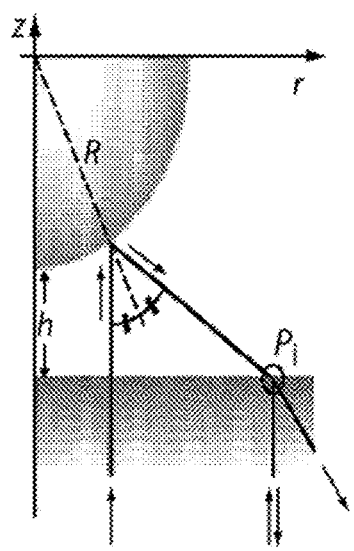
Figure 5C:
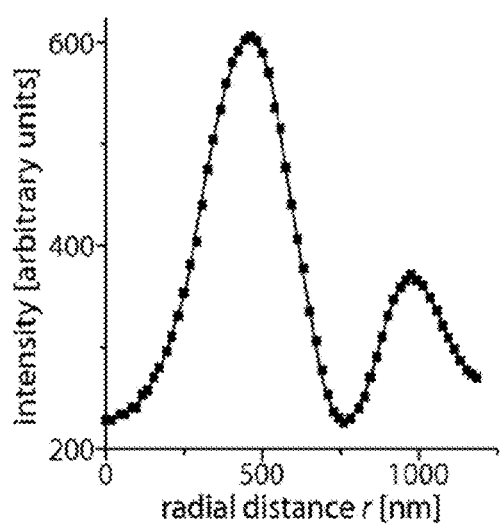
Figure 5D:
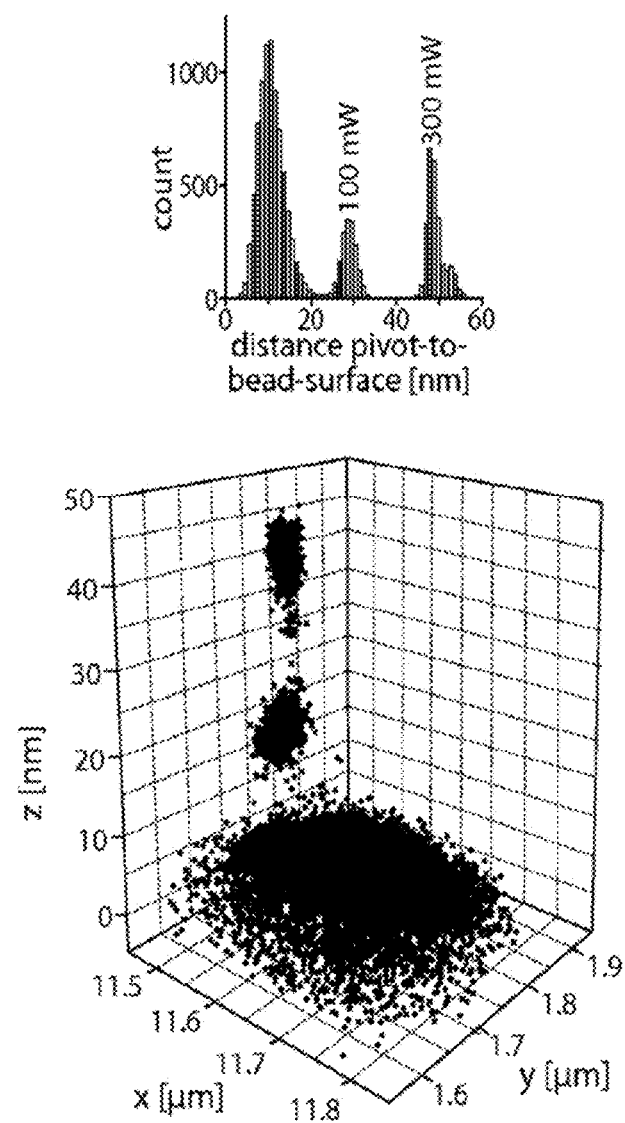

The BSD can be determined using a variety of techniques including centrifuge force microscopy (CFM), magnetic tweezers, forward scattering illumination, optical tweezers, acoustic tweezers, and the like. CFM is described in greater detail in published patent application US20130288349 and its parent patent, both of which are incorporated by reference herein. CFM is illustrated schematically in FIG. 4. CFM can be used to perform thousands of single-molecule force experiments in parallel.

One variation of CFM, referred to as RIC-CFM, incorporates reflection interference contrast microscopy (RICM) into the CFM. The imaging optics, optical models, and algorithms used to track individual microspheres in 3D with subnanometer (Angstrom) precision are shown in FIG. 5. By incorporating the necessary optics into the CFM, this approach provides subnanometer-level resolution tracking of many beads simultaneously including up to 400 beads with 2 angstrom resolution at 100 Hz (e.g., together with a modern 4 Megapixel, 100 Hz sCMOS camera), or 1 bead with 2 angstrom resolution at 10,000 Hz or more with a high-speed, low-resolution camera.

In addition, the CFM or any of the imaging techniques being used can be coupled with a fluidic control system, such as a microfluidic control system, in order to facilitate the introduction and removal of nucleic acids and denaturing agents used in the methods described herein. Still further, a high-speed translation stage may be added to the CFM to enable rapid scanning of the sample.

This disclosure further contemplates extending the high-resolution CFM assay to create a massively-multiplexed platform for characterizing the states of nanocaliper constructs. While the CFM assay is intrinsically highly parallel, to characterize many different nanocaliper constructs (e.g., different unique cysteine mutants) within a single assay, as opposed to multiple copies of the same construct, the method provides a means to identify each unique interaction. This is done using a barcoding technique that uses the force-extension behavior of pre-programmed DNA nanoswitches.

Figure 6:
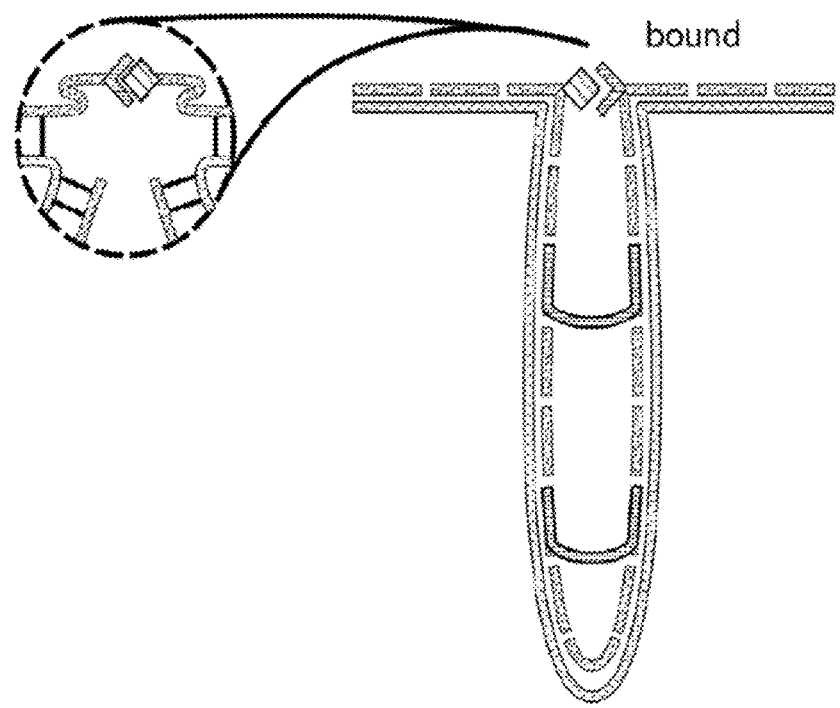
FIG. 6. Putative design of force-barcoded DNA nanoswitch, consisting of multiple nested loops that break open under force. This enables the unique identification of up to a million different nanocaliper complexes.

A large family of DNA nanoswitch constructs is constructed, each one uniquely identifiable by its force-extension behavior. In its simplest form, this family of constructs can be generated by adding loops of different sizes in series with the nanocaliper constructs, designed to break open under application of a prescribed mechanical force. The different loop sizes can be distinguished using for example CFM. Alternatively, the single DNA loop can be replaced with a collection of nested loops designed to break open under increasing force (FIG. 6). This approach will enable millions of unique barcodes, all observable in real-time in the CFM (e.g., if more than 100 different loop sizes can be distinguished, three nested loops would enable on the order of $10^6$ different combinations). This nested loop structure can serve as an alternative design for the CLP-I calipers described herein. Calibration loops could be placed in parallel, rather than in series, with the target protein, and reconfiguration of the caliper structure could be triggered by force-mediated strand melting instead of strand-displacement.

Targets

A variety of targets can be analyzed using the methods of this disclosure. The only limitation on the target is that it must be amenable to being bound to a nucleic acid directly or indirectly. The target may be without limitation a protein, a polypeptide, a peptide, a nucleic acid, a virus-like particle, a steroid, a proteoglycan, a lipid, a carbohydrate, and analogs, derivatives, mixtures, fusions, combinations or conjugates thereof.

One class of targets is peptide-based targets such as (single or multi-chain) proteins and peptides. Examples of peptide-based targets include without limitation antibodies, single chain antibodies, antibody fragments, enzymes, co-factors, receptors, ligands, transcription factors and other regulatory factors, some antigens (as discussed below), cytokines, chemokines, hormones, and the like.

In some embodiments, inorganic or synthetic agents can be analyzed. Such inorganic or synthetic agents include inorganic non-particles and synthetic polymers.

Modification of Targets

The surface of the target (e.g., multiprotein complex) may be decorated covalently with ssDNA handles to create points of attachment to the caliper. Carbodiimide activation followed by reaction with amines can be used for specific modification of aspartate and glutamate residues, although preferably lysines are consumed or protected beforehand to prevent unwanted cross-reaction. Mendoza and Vachet, Probing Protein Structure by Amin Acid-Specific Covalent Labeling and Mass Spectrometry; Mass Spectrom Rev, 28(5):785-815, 2009, report methods for amino acid specific modification of eight kinds of residues as follows:

A. arginine (e.g. reaction with phenylglyoxal)
B. carboxylate (aspartate and glutamate) (e.g. activation by carbodiimide then reaction with amino-oxy)
C. cysteine (e.g. reaction with maleimide)
D. histidine (e.g. reaction with diethylpyrocarbonate)
E. lysine (e.g. reaction with NHS ester)
F. tryptophan (e.g. reaction with 2-hydroxy-5-nitrobenzyl bromide)
G. tyrosine (e.g. reaction with tetranitromethane, iodine, or N-acetylimidazole)

If analysis of targets only in the denatured state is desired, then decoration with ssDNA handles can be done under denaturing conditions, e.g., in the presence of 6 M GuCl, 8 M urea, or 1% SDS. Therefore positions buried on the inside of the native structure can be accessible for labeling.

Applications and Uses

The methods provided herein can be used to determine (or map) the surface structure of proteins of known primary amino acid sequence. In these instances, the attachment points to a target protein will be known (due to the known reactivity and specificity of the reagents used for attachment). For example, it will be known that the attachment points are lysines because a NHS reactive group will be used to attach. Initially, the distance between the lysines is determined when the target protein is in its native conformation. This distance is used to map the surface structure of the target protein. It will not be known which specific lysines are involved, since the attachment to the target protein is random and could be to any surface lysines available for reaction. However, the target protein is then stretched under denaturing conditions (such as but not limited to in the presence of SDS), allowing the distance between the two lysines to be determined when the target protein is denatured. This latter distance will then be used to identify which lysines are involved by comparison to the known primary amino acid sequence.

The methods can also be used to determine (or map) the surface structure of a protein of unknown primary amino acid sequence. A similar approach to that described above can be used except that more iterations of the process are likely necessary. In the process, the primary amino acid sequence will also be partially determined.

The ability to identify a target allows its presence to be determined in a sample or as a result of an event. Accordingly, the methods can be used as detection or diagnostic methods to determine the presence (or absence) of a target. This may have a wide range of uses, including clinical uses.

The methods can also be used to determine changes in structure to a target as a result of binding to a known or unknown binding partner or to determine changes in structure in response to applied force(s). Typically, the target structure when in an unbound state is known or determined. Examples of binding partners include putative drug candidates such as allosteric inhibitors or activators (e.g., activators of enzymes such as kinases). In this way, the methods can be used in massively parallel drug screening assays.

The methods can also be used for single-particle detection or proteomics, for example identification of viruses. They can further be used for rapid structural characterization of synthetic-biology devices, such as artificial protein machines. More specific applications are described below.

Single-Cell Proteomics

DPC can be used to tackle a key technical challenge for cell biology: counting, spatio-temporal tracking, and structure determination of a random sampling of the proteome of a single cell. Currently this can be done to an extent for individual nucleic acids in a single cell, due to probe hybridization or sequencing based identification of them. For proteins, on the other hand, mass spectrometry or other methods fail to offer anywhere near single-molecule sensitivity on a proteome scale. In contrast, DPC can extend single-molecule identification and counting to proteins on a proteome scale by collecting a 1D sequence fingerprint on each polypeptide (or nucleic acid). This includes measurement, on a single-molecule level, of any post-translational modifications present on individual proteins (or post-transcriptional modifications on individual RNAs) that can be specifically labeled by a ssDNA handle; for example, serine/threonine phosphorylations can be targeted by beta-elimination at alkaline pH followed by Michael addition of a thiol-labeled ssDNA handle; de-acetylated lysines could be monitored by NHS-labeled ssDNA handles; antibodies or aptamers may be usable as well to direct linkage of ssDNA handles to targeted sites. Furthermore, DPC can return information about not just the identity, but also the native structure of individual macromolecular complexes in the proteome (and transcriptome) by collecting a 3D surface fingerprint of each target, thus conformational heterogeneities unrelated to chemical composition also can be monitored. Therefore, DPC can enable single-target, single-cell proteomics including information about macromolecular conformations.

Single-molecule fingerprinting of post-translational modifications by itself is an unprecedented and valuable application in of itself. Bulk methods provide a statistical picture of post-translational modifications, not the correlated modifications on single biopolymer chains.

Spatially Resolved Single-Cell Proteomics

A large number of randomly selected targets, each randomly barcoded with a unique ssDNA tag, can be tracked through space and time within a single cell using DPC. Temporal resolution as well may be possible by pulse labeling with time-encoding barcodes. One can tag proteins within a single-cell with randomly selected barcodes serving as unique identifiers, and track the position in space and time of these barcodes using super-resolution microscopy. Then one could extract all proteins from that cell, and then use DPC to identify each barcode along with the 3D surface profile of the target tagged by that barcode, as well as the 1D sequence fingerprints of the polypeptides present in that target. Thus, spatiotemporally resolved single-cell proteomics can be enabled by DPC.

Single-Molecule Nucleic Acid Sequencing, Including Sequencing of Repeat Regions

The calipers and methods provided herein can be used for nucleic acid (e.g., DNA) sequencing. Below is process that can be used to sequence nucleic acids. The sequencing methods can be used to detect and identify "dark regions" of genomes. "Dark regions" of genomes are regions that remain unamenable to DNA sequencing, typically because they bear high levels of repeats. DPC can be used for two key operations in single-molecule DNA sequencing, especially for reading repeat regions. These key operations are (1) readout of the precise distance between barcoded sequence tags attached to the target DNA; and (2) readout of the sequence identity of the barcoded sequence tags. This can be accomplished as follows:

1. Provide a population (or plurality) of target DNA
2. Perform one round (or cycle) of polymerase copying incorporating deoxyuridine into one strand, but not the other
3. Introduce 1 nt gaps by treating the nucleic acid with uracil DNA glycosylase
4. Widen one or more of the gaps with exonuclease
5. Ligate into one or more of the gaps barcoded, crosslinkable, end-protected 5mers
6. Crosslink the 5mers to the template strand to create barcode-studded target DNAs
7. Capture the barcode-studded target DNAs on calipers (i.e., each caliper grabs two barcodes at random)
8. Read out the distance between the barcodes, and then read out the identity of each barcode
9. Release one barcode, grab another barcode, and repeat; in this way, obtain the pairwise distances and identities of many barcodes on a single barcode-studded target DNA
10. If desired, go through another round of ligation of barcoded 5mers by deprotecting the end of the 5mers, then ligating another set DPC can be used to localize barcodes to 1 bp accuracy per 1 kb. This can be accomplished, for example, by applying a large force (e.g., up to 1 nN or more particularly under dry conditions such as in air or in organic solvent to prevent force-coupled hydrolysis). By doing so, it may be possible to achieve 0.1% accuracy for the distance between 5mer barcodes (e.g., within 1 base on a 1 kilobase target).

Single-Molecule Fingerprinting of Polysaccharides

In this application, individual saccharide (or sugar) monomers, within a polysaccharide, are labeled with handles having embedded therein barcodes that encode information about the type of sugar, randomly selected identifier, etc. Then, pairwise distances between handles are measured.

Target Identification Using Fingerprinting

DPC can be used to determine the identity and/or the quantity of targets of interest (including small targets of interest), such as proteins, DNA constructs, viruses, other macromolecules, etc., by generating distance fingerprints of targets within a sample. Each fingerprint will consist of multiple distance measurements made on a single target. These measurements can be made in a similar way as previously described for the structure determination application. For example, the following steps can be carried out:

i) multiple nucleic acid (e.g., DNA) handles are attached to targets of interest within a sample, with each handle potentially including a barcode;

ii) handle-labelled targets are attached to DPC constructs;

iii) target-coupled DPC constructs are attached as tethers between beads and surfaces to enable single-molecule distance measurements;

iv) multiple, distance measurements are made on each caliper through repeated cycles of handle-attachment, distance measurement, and handle detachment.

These steps need not be carried out in the order shown above. For example, the calipers could be attached to beads prior to attachment to targets to be identified.

This application is a simplified method as compared to that described above for structure determination, partly because it does not require as much information to be obtained from each sample since the goal is not to determine a de novo structure but simply to identify the target (the structure or "fingerprint" of which may already be known). Furthermore, the computational requirements are much lower than for structure determination, since the method requires comparing the distance fingerprint of each sample target against a database of fingerprints to identify the target. The identification database could be generated by actually making measurements on a wide variety of known targets using the methods provided herein, or by computational methods based on known structure.

Protein fingerprinting and identification could be performed on both folded, native structures, as well as on denatured structures. When fingerprinting denatured proteins, the experimental requirements are relaxed in a number of ways: (1) since the protein is already denatured, there is no concern about denaturing it with the forces applied in performing the methods described herein. This allows the use of even higher forces which in turn can reduce thermal noise. (2) The resolution requirements are lower as single-amino-acid resolution (~3-4 Angstroms) is all that is needed, and probabilistic identification could be performed with even lower resolution. (3) A wider range of buffer and environmental conditions could be used (e.g., salt, pH, temperature, etc.), with some denaturant such as SDS or urea potentially included to keep the peptides denatured. (4) Even if the protein is fragmented we could potentially still identify the protein using similar algorithms as used for mass spectrometry proteomics.

As the approach provided herein works at a single molecule level, target identification and profiling can be performed on very small volumes, including i) lysate from a single-cell, and ii) small volume samples such as but not limited to small volumes of bodily fluids such as blood, urine and saliva. Thus, DPC can be applied to single-cell proteomics and ultra-low volume detection.

It should also be noted that all strand displacement actuations described herein can be mediated by incorporating a toehold domain into the strand being removed.

High-Throughput, Single-Molecule Macromolecular Structure Determination

The 3D surface fingerprints of macromolecular complexes that are measured via DPC can be used to refine backbone structural models of these complexes, or in some cases may provide sufficient experimental restraints for de novo backbone structure determination without any additional experimental data. Furthermore, the stiffness and force-dependent conformational transitions can be measured for force applied at pairs of surface points, and in this way additional information can be obtained relating to macromolecular complexes.

Because DPC is high-throughput, it can be used to measure 3D surface fingerprints for complex mixtures of targets. For example, one could generate a library of recombinant versions of a protein, each with a different set of mutations, each with a barcode attached that encodes information about the genotype. Furthermore, one could repeat 3D surface fingerprinting for mixtures under varying environmental conditions, such as pH, temperature, salt concentrations, presence of detergents, presence of denaturants, external fields, presence of varying ligands, presence of macromolecular binding partners. This only is possible for methods having sufficiently high throughput, as does DPC.

As described in part herein, structural determination contemplates attaching the caliper to a variety of handles on the target. Several such measurements may be made between handles attached to the same protein. Handles may include a barcode such that each handle may be uniquely identified and positioned. Where the structure of the protein is known, the binding sites can be mapped to that known structure. Furthermore, it is possible to analyze and identify structural heterogeneity in a population of macromolecules (or complexes) due to the high-resolution structural detailed that can be obtained using DPC.

The high-throughput nature of the analysis also facilitates obtaining structural information on libraries, e.g. every single or double mutation, particularly since it is possible to barcode the identity of each member of the library. There are also variants that can be changed in order to further the analysis. These include changes in salts, temperature, pressure, ligands, chemical modifications, binding partners, degradation, force, and the like.

The methods provided herein can also be used for fitting structural models. Such models may be generated using structural determination processes, such as but not limited to those provided herein. Such models can then be scored against experimental data obtained using the methods provided herein. This process may yield additional data to score against that is not present in static structures, for example it may provide information relating to folding and unfolding of targets such as proteins or macromolecular structures. The data generated using the methods provided herein also yield information about the response and compliance of a target under force or other environmental condition. These are properties cannot be studied using static structure analysis. It is also possible to better distinguish between a correct static model and a decoy static model (i.e., a similar model but with subtle defects) based on fitting to the material properties that can be measured using the methods provided herein.

Footprinting

Footprinting, as used herein, is a process that allows the identification of regions on a target that are not available for modification by probes such as the handles used in DPC. By observing which residues cannot be labeled by the handles, one can deduce what residues are unavailable, potentially because they are located on the inside of the target, or potentially due to chemical blocking (e.g., acetylation of lysines). DPC enables single-molecule footprinting, thereby identifying hidden residues in or on single targets.

Mapping Allosteric Interfaces and Transitions

The methods provided herein can also be used to study and/or identify conformational changes that are induced by force application, or any other perturbations (e.g., ligands, salts, temperature, and the like). This allows different conformational states and their inducers to be identified and correlated. The methods can also be used to study and/or identify the effects including structural effects of one or more point mutations of the target. This in turn can be used to identify sites for allosteric drugs or agents on therapeutic targets.

Single-Molecule Pulldown: Determining Binding Partners for Ligands, and the Structure of the Formed Complexes Important challenges in drug discovery are as follows: (1) determine the identity of therapeutic targets (including off-targets) of drugs, (2) determine the kinetics and thermodynamics of drug:target interaction, (3) determine the structure of the drug:target complex, (4) determine drug-induced conformational changes in the target.

For determining the identity of targets, a typical strategy is to couple the drug to a solid support, bind the target, elute the target, and then identify the target using mass spectrometry or related method. This process however cannot identify targets at the single-molecule detection limit. It also does not provide information relating to the remaining challenges. DPC, on the other hand, is able to achieve all four steps. In DPC, the caliper is tethered to both the drug and a random site on the target, the distance between these two attachments is determined, and then the target and the random site on the target are identified. As described in the Target Identification via Fingerprinting section herein, multiple rounds of attaching and stretching at low force or high force could be used to determine a 3D native fingerprint or a 1D sequence fingerprint respectively. To do this, the drug can be tagged with a nucleic acid (e.g., DNA) handle. Alternatively, if interference with drug-target binding is a concern, the drug may be tagged with a smaller tag (e.g., azide click tag) as well as a crosslinkable moiety (e.g., amine reactive tether) that is used to crosslink the drug to the target. After crosslinking the drug through the tether to the target, the handle could be attached to the azide click tag.

Super Resolution Microscopy

DPC also can be used as an alternative to standard approaches for super resolution imaging. Instead of using the localization of a fluorophore to identify the position of a feature of interest, the positions of small beads attached to features of interest would be tracked via nucleic acid (e.g., DNA) handles. This provides a number of advantages compared to standard fluorescence assays. The positions of the beads can be measured at high-resolution in 3D. We have already demonstrated bead tracking resolutions of ~1 nm in x and y and ~0.2 nm in z per 100 fps video frame, which exceeds the resolution of current super-resolution techniques, due to the higher signal-to-noise, lack of bleaching, etc. of bead tracking versus fluorescence imaging. Each bead could report the position of many different DNA-labeled sites, through multiple cycles of detachment from one DNA-labeled site and attachment to another DNA-labeled site. Furthermore, bead positions can be measured under the application of force (or changing forces), which could serve to both decrease the thermal noise of the beads thereby increasing resolution, as well as to measure the compliance and force-dependent deformations of the objects under observation. Different barcodes could also be integrated into the handles to enable identification and localization of different types of sites. Furthermore, due to the huge number of different barcodes that can be created and identified (e.g., more than 1 million), it will be possible to distinguish many more features than can be accomplished with fluorescence imaging currently.

Nucleic Acid Nanostructure Methodology Generally

The structural determination methodology described herein may be applied to any number and type of nucleic acid nanostructures. Nucleic acid nanostructures may be synthesized using any variety of nucleic acid folding methods including but not limited to DNA origami and DNA single stranded tiles (SST). One such approach is DNA origami (Rothemund, 2006, Nature, 440:297-302, incorporated herein by reference in its entirety). In a DNA origami approach, a structure is produced by the folding of a longer "scaffold" nucleic acid strand through its hybridization to a plurality of shorter "staple" oligonucleotides, each of which hybridize to two or more non-contiguous regions within the scaffold strand. In some embodiments, a scaffold strand is at least 100 nucleotides in length. In some embodiments, a scaffold strand is at least 500, at least 1000, at least 2000, at least 3000, at least 4000, at least 5000, at least 6000, at least 7000, or at least 8000 nucleotides in length. The scaffold strand may be naturally or non-naturally occurring. The scaffold typically used in the M13mp18 viral genomic DNA, which is approximately 7 kb. Other single stranded scaffolds may be used including for example lambda genomic DNA. Staple strands are typically less than 100 nucleotides in length; however, they may be longer or shorter depending on the application and depending upon the length of the scaffold strand. In some embodiments, a staple strand may be about 15 to about 100 nucleotides in length. In some embodiments the staple strand is about 25 to about 50 nucleotides in length.

These techniques are known in the art, and are described in greater detail in U.S. Pat. Nos. 7,745,594 and 7,842,793; U.S. Patent Publication No. 2010/00696621; and Goodman et al. Nature Nanotechnology.

In some embodiments, a nucleic acid structure may be assembled in the absence of a scaffold strand (e.g., a scaffold-free structure). For example, a number of oligonucleotides (e.g., <200 nucleotides or less than 100 nucleotides in length) may be assembled to form a nucleic acid nanostructure. This approach is described in WO 2013/022694 and WO 2014/018675, each of which is incorporated herein by reference in its entirety.

Other methods for assembling nucleic acid structures are known in the art, any one of which may be used herein. (See for example Kuzuya and Komiyama, 2010, Nanoscale, 2:310-322.) It is also to be understood that a combination or hybrid of these methods may also be used to generate the nucleic acid structures disclosed herein.

Nucleic Acids

The nucleic acid structures may comprise naturally occurring and/or non-naturally occurring nucleic acids. If naturally occurring, the nucleic acids may be isolated from natural sources or they may be synthesized apart from their naturally occurring sources. Non-naturally occurring nucleic acids are synthetic.

The terms "nucleic acid", "oligonucleotide", and "strand" are used interchangeably to mean multiple nucleotides attached to each other in a contiguous manner. A nucleotide is a molecule comprising a sugar (e.g. a deoxyribose) linked to a phosphate group and to an exchangeable organic base, which is either a pyrimidine (e.g., cytosine (C), thymidine (T) or uracil (U)) or a purine (e.g., adenine (A) or guanine (G)). In some embodiments, the nucleic acid may be L-DNA. In some embodiments, the nucleic acid is not RNA or an oligoribonucleotide. In these embodiments, the nucleic acid structure may be referred to as a DNA structure. A DNA structure however may still comprise base, sugar and backbone modifications.

Modifications

A nucleic acid structure may be made of DNA, modified DNA, and combinations thereof. The oligodeoxyribonucleotides (also referred to herein as oligonucleotides, and which may be staple strands, connector strands, and the like) that are used to generate the nucleic acid structure or that are present in the nucleic acid structure may have a homogeneous or heterogeneous (i.e., chimeric) backbone. The backbone may be a naturally occurring backbone such as a phosphodiester backbone or it may comprise backbone modification(s). In some instances, backbone modification results in a longer half-life for the oligonucleotides due to reduced nuclease-mediated degradation. This is turn results in a longer half-life. Examples of suitable backbone modifications include but are not limited to phosphorothioate modifications, phosphorodithioate modifications, p-ethoxy modifications, methylphosphonate modifications, methylphosphorothioate modifications, alkyl- and aryl-phosphates (in which the charged phosphonate oxygen is replaced by an alkyl or aryl group), alkylphosphotriesters (in which the charged oxygen moiety is alkylated), peptide nucleic acid (PNA) backbone modifications, locked nucleic acid (LNA) backbone modifications, and the like. These modifications may be used in combination with each other and/or in combination with phosphodiester backbone linkages.

Alternatively or additionally, the oligonucleotides may comprise other modifications, including modifications at the base or the sugar moieties. Examples include nucleic acids having sugars which are covalently attached to low molecular weight organic groups other than a hydroxyl group at the 3' position and other than a phosphate group at the 5' position (e.g., a 2'-O-alkylated ribose), nucleic acids having sugars such as arabinose instead of ribose. Nucleic acids also embrace substituted purines and pyrimidines such as C-5 propyne modified bases (Wagner et al., *Nature Biotechnology* 14:840-844, 1996). Other purines and pyrimidines include but are not limited to 5-methylcytosine, 2-aminopurine, 2-amino-6-chloropurine, 2,6-diaminopurine, hypoxanthine. Other such modifications are well known to those of skill in the art.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863, and alkylphosphotriesters (in which the charged oxygen moiety is alkylated as described in U.S. Pat. No. 5,023,243 and European Patent No. 092574) can be prepared by automated solid phase synthesis using commercially available reagents. Methods for making other DNA backbone modifications and substitutions have been described (Uhlmann, E. and Peyman, A., Chem. Rev. 90:544, 1990; Goodchild, J., *Bioconjugate Chem.* 1:165, 1990).

Nucleic acids can be synthesized de novo using any of a number of procedures known in the art including, for example, the b-cyanoethyl phosphoramidite method (Beaucage and Caruthers *Tet. Let.* 22:1859, 1981), and the nucleoside H-phosphonate method (Garegg et al., *Tet. Let.* 27:4051-4054, 1986; Froehler et al., *Nucl. Acid. Res.* 14:5399-5407, 1986; Garegg et al., *Tet. Let.* 27:4055-4058, 1986, Gaffney et al., *Tet. Let.* 29:2619-2622, 1988). These chemistries can be performed by a variety of automated nucleic acid synthesizers available in the market. These nucleic acids are referred to as synthetic nucleic acids. Modified and unmodified nucleic acids may also be purchased from commercial sources such as IDT and Bioneer.

Isolation, as used herein, refers to the physical separation of the desired entity (e.g., nucleic acid structures, etc.) from the environment in which it normally or naturally exists or the environment in which it was generated. The isolation may be partial or complete. An isolated nucleic acid generally refers to a nucleic acid that is separated from components with which it normally associates in nature. As an example, an isolated nucleic acid may be one that is separated from a cell, from a nucleus, from mitochondria, or from chromatin.

The nucleic acid nanostructures may be isolated and/or purified. Isolation of the nucleic acid nanostructure may be carried out by running a hybridization reaction mixture on a gel and isolating nucleic acid structures that migrate at a particular molecular weight and are thereby distinguished from the nucleic acid substrates and the spurious products of the hybridization reaction. As another example, isolation of nucleic acid structures may be carried out using a buoyant density gradient, sedimentation gradient centrifugation, or through filtration means.

REFERENCES

1. Pinheiro A V, Han D, Shih W M, Yan H. Challenges and opportunities for structural DNA nanotechnology. *Nat Nanotechnol.* 6, 763-72, 2011.
2. Halvorsen K, Wong W P. Massively parallel single-molecule manipulation using centrifugal force. *Biophys J.* 98, L53-55, 2010.
3. Otto O, Czerwinski F, Gornall J L, Stober G, Oddershede L B, Seidel R, Keyser U F. Real-time particle tracking at 10,000 fps using optical fiber illumination. Opt. Express, 18, 22722-22733, 2010.
4. Lansdorp, B. M., Tabrizi, S. J., Dittmore, A., & Saleh, O. A. A high-speed magnetic tweezer beyond 10,000 frames per second. *Review of Scientific Instruments,* 84, 044301-044301, 2013.
5. Heinrich V, Wong W P, Halvorsen K, Evans E. Imaging biomolecular interactions by fast three-dimensional tracking of laser-confined carrier particles. *Langmuir* 24, 1194-1203, 2008.
6. Kim K, Saleh O A. A high-resolution magnetic tweezer for single-molecule measurements. *Nucleic Acids Research,* 37, e136-e136, 2009.

What is claimed is:

1. A system comprising
   (a) a single-stranded nucleic acid caliper having a reference domain and a target domain, wherein from 5' to 3' or 3' to 5' the single-stranded nucleic acid caliper comprises
      (1) a reference domain comprising
         (i) a nucleotide sequence RS2 that is complementary to a reference splint,
         (ii) a nucleotide sequence RR2 that is complementary to a nucleic acid handle RH2 that flanks a reference molecule,
         (iii) a reference domain sequence,
         (iv) a nucleotide sequence RR1 that is complementary to a nucleic acid handle RH1 that flanks the reference molecule, and
         (v) a nucleotide sequence RS1 that is complementary to the reference splint; and
      (2) a target domain comprising
         (i) a nucleotide sequence TS2 that is complementary to a target splint,
         (ii) a nucleotide sequence TT2 that is complementary to a nucleic acid handle TH2 that flanks a target,
         (iii) a target domain sequence,
         (iv) a nucleotide sequence TT1 that is complementary to a nucleic acid handle TH1 that flanks the target, and
         (v) a nucleotide sequence TS1 that is complementary to the target splint;
   (b) the reference splint that is a single-stranded oligonucleotide comprising partial sequence complementarity to the single-stranded nucleic acid caliper at the nucleotide sequences RS2 and RS1, and a RS toehold sequence that remains single-stranded when the reference splint is bound to the single-stranded nucleic acid caliper;
   (c) the target splint that is a single-stranded oligonucleotide comprising partial sequence complementarity to the single-stranded nucleic acid caliper at the nucleotide sequences TS2 and TS1, and a TS toehold sequence that remains single-stranded when the target splint is bound to the single-stranded nucleic acid caliper; and
   (d) a reference molecule flanked by two single-stranded nucleic acid handles, RH1 and RH2,
   wherein the reference domain is configured to form a loop when hybridized to the reference splint and/or the reference molecule, and the target domain is configured to form a loop when hybridized to the target splint and/or to the target; and
   wherein the nucleic acid caliper is configured to be attached to a solid surface.

2. The system of claim 1, further comprising the target flanked by two single-stranded nucleic acid handles, TH1 and TH2.

3. The system of claim 1, wherein the single-stranded caliper is conjugated to a bead at a first end.

4. A method of use of the system of claim 1 comprising
(a) measuring, under tension, a bead-to-surface distance of the nucleic acid caliper of claim 1 attached to a surface on a first end and to a bead on a second end, when bound to the reference molecule, the target flanked by single-stranded nucleic acid handles TH1 and TH2, and the target splint but not bound to a reference splint (BSD-ref),
(b) removing the target splint from the nucleic acid caliper and hybridizing the reference splint to the nucleic acid caliper,
(c) measuring, under tension, the bead-to-surface distance of the nucleic acid caliper, when bound to the reference molecule, the target flanked by single-stranded nucleic acid handles TH1 and TH2, the reference splint but not bound to the target splint (BSD-target), and
(d) determining the difference between BSD-target and BSD-ref as a measure of the distance between points of attachment of the single-stranded nucleic acid handles bound to the target when the target is in its native (non-denatured) conformation.

5. The method of claim 4, further comprising measuring, under tension and denaturing conditions, the bead-to-surface distance of the nucleic acid caliper, when bound to the target, the reference molecule and the reference splint, to obtain the distance between points of attachment of the single-stranded nucleic acid handles bound to the target when the target is in its denatured conformation.

6. The method of claim 4, wherein the target is a protein.

7. The method of claim 4, wherein the target is a nucleic acid nanostructure.

8. The method of claim 7, further comprising measuring, under tension and in the presence of a first displacement nucleic acid, the bead-to-surface distance of the nucleic acid caliper, when bound to the target, the reference molecule, the reference splint, and the first displacement nucleic acid, to identify a first point of attachment of the single-stranded nucleic acid handles to the target.

9. The method of claim 8, further comprising measuring, under tension and in the presence of a second displacement nucleic acid, the bead-to-surface distance of the nucleic acid caliper, when bound to the target, the reference molecule, the reference splint, and the second displacement nucleic acid, to identify a second point of attachment of the single-stranded nucleic acid handles to the target.

10. The system of claim 1, wherein the single-stranded caliper is conjugated to a bead at a first end and to a surface at a second end.

11. The system of claim 10, wherein the bead is a microbead.

12. The system of claim 10, wherein the bead is a magnetic bead.

13. The system of claim 1, wherein the caliper is attached to a fixed surface.

14. The system of claim 1, further comprising a RS displacement strand that is complementary to the sequence of the RS toehold sequence.

15. The system of claim 1, further comprising a TS displacement strand that is complementary to the sequence of the TS toehold sequence.

16. The system of claim 1, wherein the target is a protein.

17. The system of claim 1, wherein the target is a protein of known primary amino acid sequence.

18. The system of claim 1, wherein the target is a protein of unknown primary amino acid sequence.

19. The system of claim 1, wherein the target is a protein bound to a binding partner.

20. The system of claim 1, wherein the single-stranded handles, TH1 and TH2, are attached to the target at unmodified surface lysines.

21. The system of claim 1, wherein the target is a nucleic acid nanostructure.

22. The system of claim 1, wherein the single-stranded handles, TH1 and TH2, each comprise a hairpin barcode sequence and a loop sequence, wherein the hairpin barcode sequence is identical between TH1 and TH2, and the loop sequence is of different length between TH1 and TH2.

23. The system of claim 1, wherein the single-stranded handles, TH1 and TH2, each comprise a barcode sequence.

24. The system of claim 23, wherein the barcode sequence is accessible via strand displacement.

25. The system of claim 23, wherein the barcode sequence is present in a nested loop.

26. A plurality of systems of claim 1, wherein the reference molecule, the reference splint, the RS1, RS2, RH1, RH2, RR1, RR2, TS1, TS2, TT1, TT2, TH1, TH2, TS toehold and RS toehold are identical between species in the plurality.

27. The plurality of systems of claim 26, wherein the single-stranded nucleic acid calipers are attached to a surface at a first end and to a bead at a second end.

28. The plurality of systems of claim 26, wherein the single-stranded nucleic acid calipers each comprises a unique sequence that forms a unique length looped structure.

* * * * *